(12) United States Patent
Carr et al.

(10) Patent No.: US 12,006,453 B2
(45) Date of Patent: Jun. 11, 2024

(54) GEL ELASTOMER FASTENING DEVICE

(71) Applicant: Pittsburgh Plastics Manufacturing, Inc., Butler, PA (US)

(72) Inventors: Casey Carr, Glenshaw, PA (US); Tanner Jack Kennedy, Pittsburgh, PA (US); George A Paleos, Pittsburgh, PA (US); Jeffrey Allen Sleigher, Butler, PA (US)

(73) Assignee: Pittsburgh Plastics Manufacturing, Inc., Butler, PA (US)

( * ) Notice: Subject to any disclaimer, the term of this patent is extended or adjusted under 35 U.S.C. 154(b) by 102 days.

(21) Appl. No.: 17/369,118

(22) Filed: Jul. 7, 2021

(65) Prior Publication Data

US 2023/0019675 A1   Jan. 19, 2023

(51) Int. Cl.
*C09J 7/29* (2018.01)
*A61G 13/12* (2006.01)
*B32B 3/26* (2006.01)
*B32B 7/06* (2019.01)
(Continued)

(52) U.S. Cl.
CPC ............ *C09J 7/29* (2018.01); *A61G 13/121* (2013.01); *A61G 13/1235* (2013.01); *A61G 13/1245* (2013.01); *A61G 13/126* (2013.01); *B32B 3/26* (2013.01); *B32B 7/06* (2013.01); *B32B 7/12* (2013.01); *B32B 27/065* (2013.01); *B32B 27/08* (2013.01); *B32B 27/40* (2013.01); *C09J 7/40* (2018.01); *A61G 13/12* (2013.01); *B32B 2266/0278* (2013.01); *B32B 2266/12* (2016.11);
(Continued)

(58) Field of Classification Search
CPC .................................................... A61G 13/127
See application file for complete search history.

(56) References Cited

U.S. PATENT DOCUMENTS 6,047,420 A * 4/2000 Priester, III ............ A61G 13/12
                                                            5/632
6,548,728 B1   4/2003 Faries, Jr. et al.
(Continued)

OTHER PUBLICATIONS

"Devon TM Foam Positioners," Web page <https://www.cardinalhealth.com/en/product-solutions/medical/surgical/or-positioning/devon-foam-positioners.html>, 3 pages, retrieved Mar. 31, 2021.
(Continued)

*Primary Examiner* — Frank D Ducheneaux
(74) *Attorney, Agent, or Firm* — Dovas Law, P.C.

(57) ABSTRACT

A user positioning apparatus is provided including a malleable pad including a first gel elastomer. The first gel elastomer is releasably connectable to the second gel elastomer, and an adhesive layer is connected to the second gel elastomer. Further provided is a user positioning method. The user positioning method includes providing a malleable pad including a first gel elastomer, providing a platform, connecting the malleable pad to the platform via the first gel elastomer, providing a user, and positioning a body part of the user on the malleable pad. Further provided are a releasable fastening system, a releasable band, and a method for connecting a user to a platform. Further provided is a user positioning device including a malleable pad including a gel elastomer, the gel elastomer including a reaction product of a composition including an isocyanate prepolymer and a polyether polyol.

35 Claims, 23 Drawing Sheets

(51) Int. Cl.
  *B32B 7/12*   (2006.01)
  *B32B 27/06*  (2006.01)
  *B32B 27/08*  (2006.01)
  *B32B 27/40*  (2006.01)
  *C09J 7/38*   (2018.01)
  *C09J 7/40*   (2018.01)
  *C09J 133/08* (2006.01)

(52) U.S. Cl.
  CPC ..... *B32B 2307/748* (2013.01); *B32B 2405/00* (2013.01); *C09J 2203/37* (2020.08); *C09J 2301/122* (2020.08); *C09J 2301/162* (2020.08); *C09J 2301/302* (2020.08); *C09J 2400/243* (2013.01); *C09J 2433/00* (2013.01); *C09J 2475/006* (2013.01)

(56) References Cited

U.S. PATENT DOCUMENTS

| | | | |
|---|---|---|---|
| 7,063,877 B2 | 6/2006 | Kurth et al. | |
| 8,615,903 B2 | 12/2013 | Zona | |
| 9,138,087 B2* | 9/2015 | Mobley | A61G 7/1084 |
| 9,228,047 B2 | 1/2016 | Motta et al. | |
| 9,840,575 B2 | 12/2017 | Srivastava et al. | |
| 10,316,132 B2 | 6/2019 | Cocconi et al. | |
| 10,435,500 B2 | 10/2019 | Srivastava et al. | |
| 10,759,919 B2 | 9/2020 | Peterson et al. | |
| 2011/0048429 A1* | 3/2011 | Callahan | A61G 13/1265 128/845 |
| 2021/0186228 A1* | 6/2021 | Martens | A47C 27/144 |

OTHER PUBLICATIONS

"Disposable Foam Positioners," Web page <https://www.universalmedicalinc.com/all-products/patient-positioning/disposable-foam-positioners.html?product_list_limit=48>, 6 pages, retrieved Mar. 31, 2021.

"GellyGrippers," Web page <https://www.gelpro.com/gelly-grippers-mat-grippers>, 6 pages, retrieved May 6, 2021.

* cited by examiner

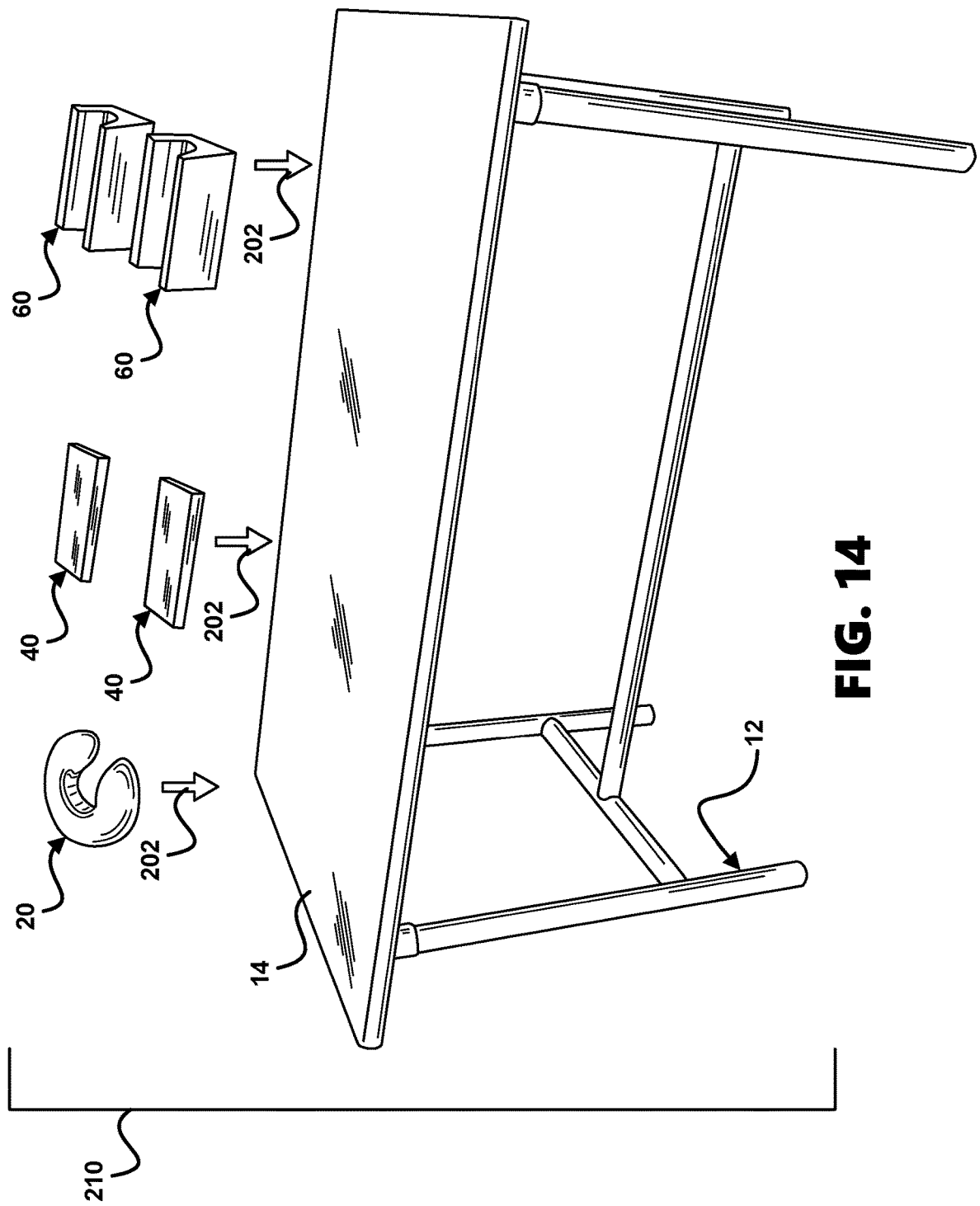

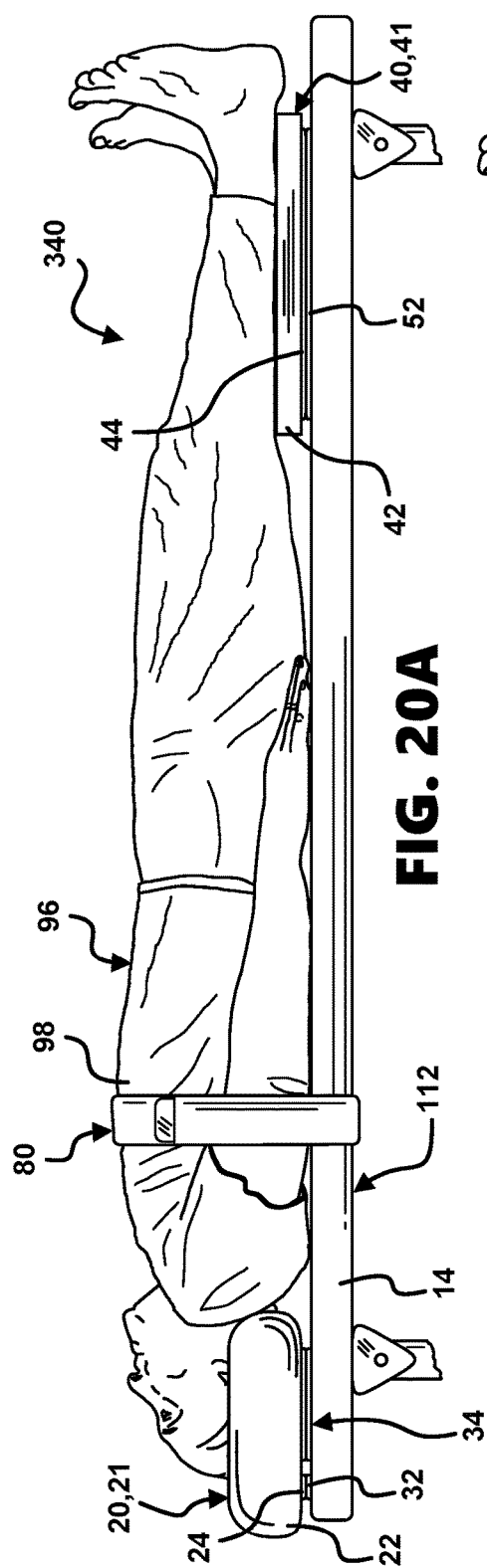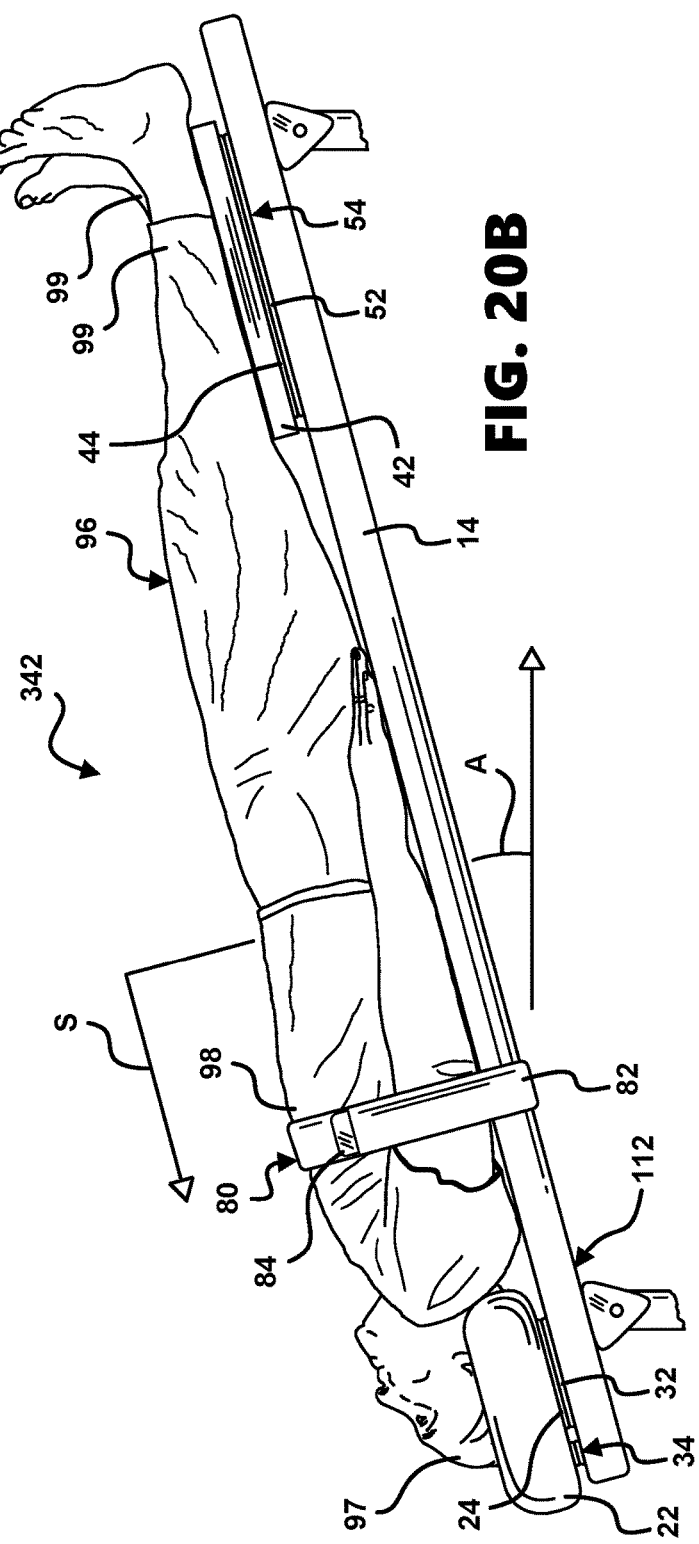

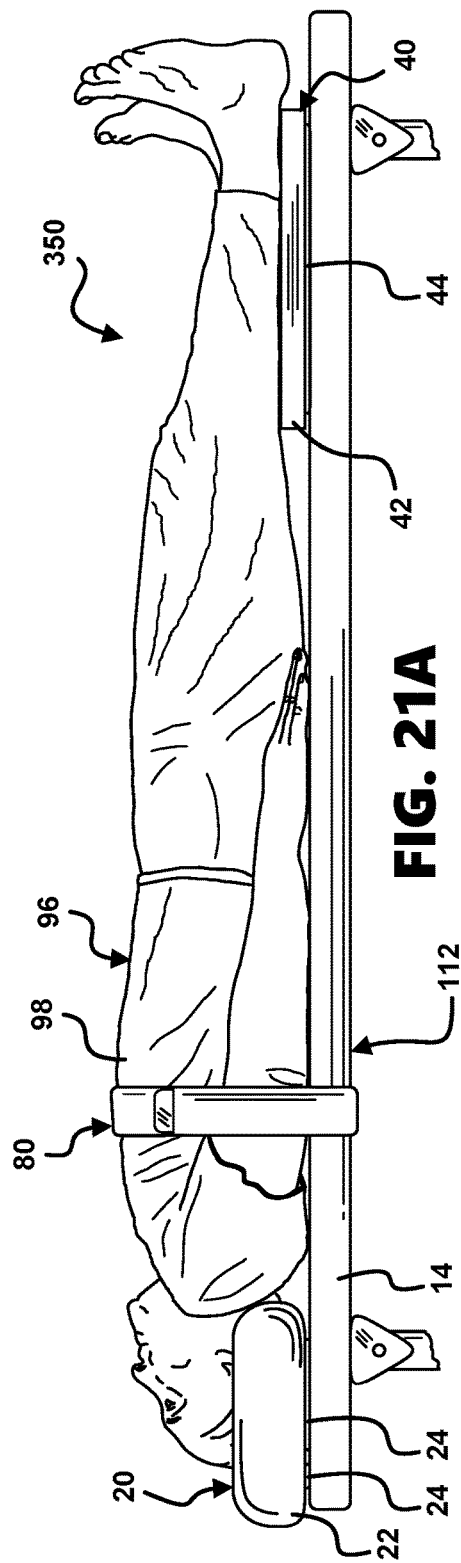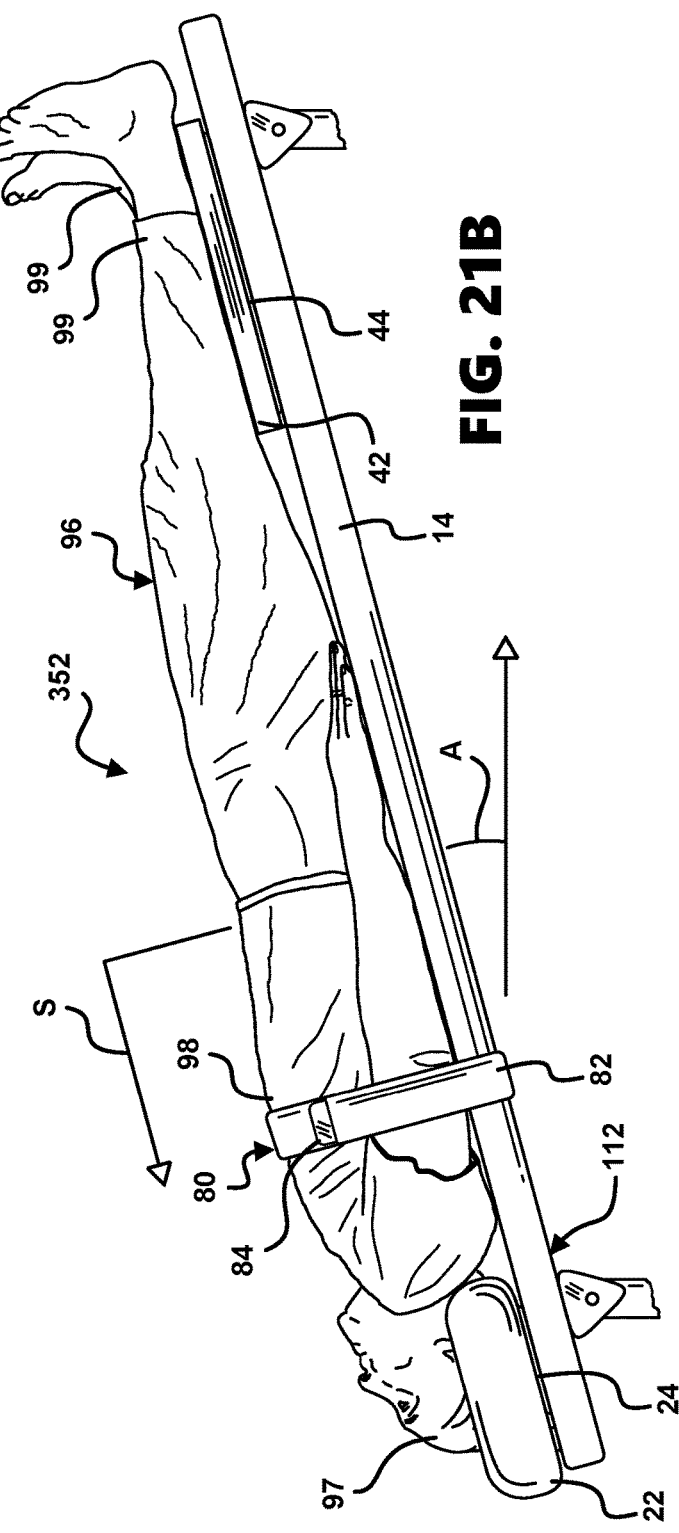

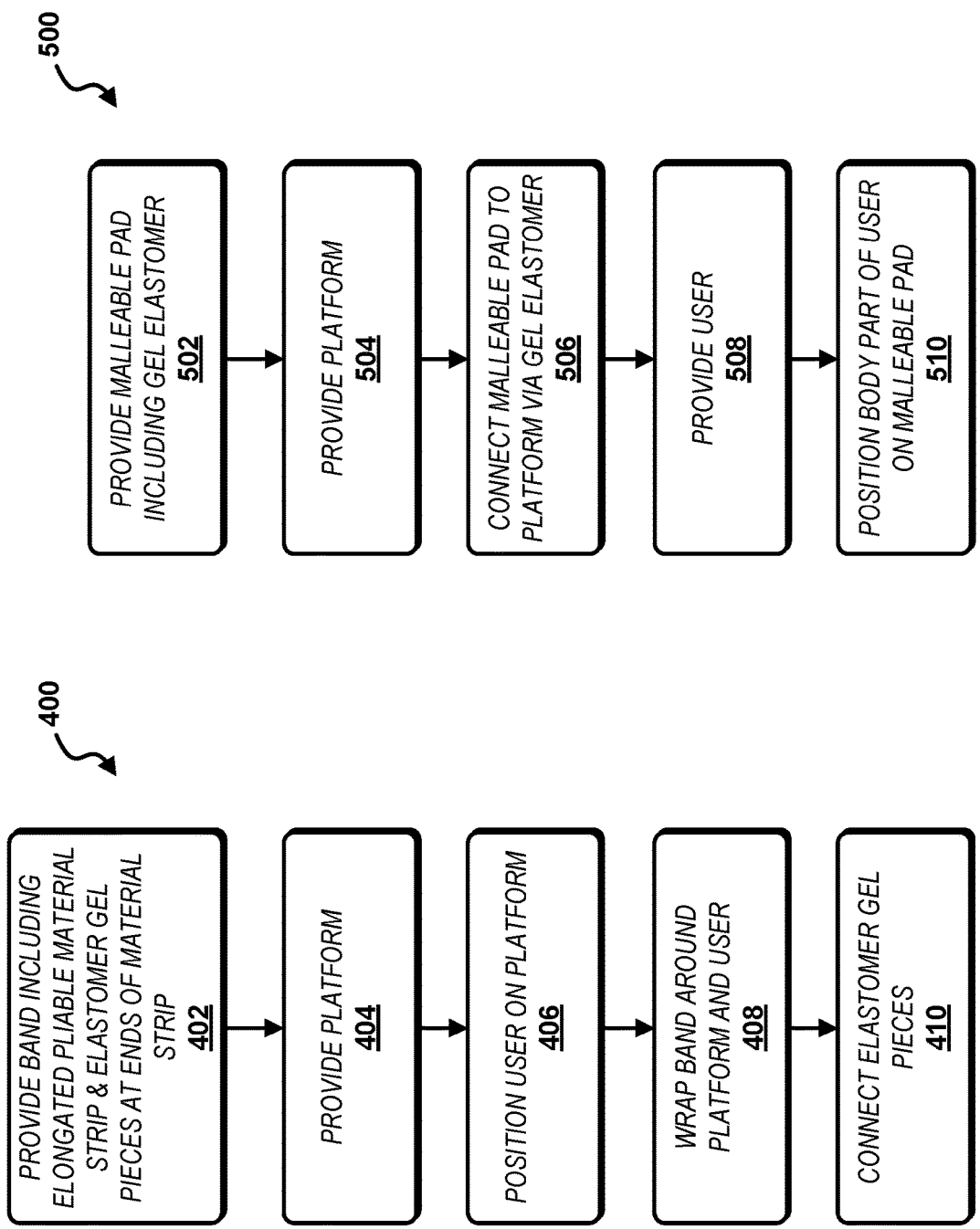

GEL ELASTOMER FASTENING DEVICE

FIELD OF INVENTION

The invention relates generally to fastening devices, and more particularly to releasable fastening devices.

BACKGROUND

Fastening devices are employed in every industry and operating environment. Releasable fastening devices in particular are required in a great plurality of applications. Hook and loop releasable fasteners are particularly well known and used in many circumstances especially in the medical field. A variety of medical devices including braces, splints, monitors, and patient positioning and fixation devices incorporate hook and loop components to allow medical professionals and capable patients themselves to efficiently attach and remove devices.

SUMMARY

This Summary introduces simplified concepts that are further described below in the Detailed Description of Illustrative Embodiments. This Summary is not intended to identify key features or essential features of the claimed subject matter and is not intended to be used to limit the scope of the claimed subject matter.

A user positioning apparatus is provided including a malleable pad including a first gel elastomer. The user positioning apparatus further includes a second gel elastomer. The first gel elastomer is releasably connectable to the second gel elastomer. An adhesive layer is connected to the second gel elastomer.

A user positioning device is provided including a malleable pad including a gel elastomer, the gel elastomer including a reaction product of a composition including an isocyanate prepolymer and a polyether polyol.

A user positioning method is provided. The user positioning method includes providing a malleable pad including a first gel elastomer and providing a platform. The malleable pad is connected to the platform via the first gel elastomer. A user is provided, and a body part of the user is positioned on the malleable pad.

A releasable fastening system is provided. The system includes a first gel elastomer sheet including a first surface and a second surface. A first adhesive layer is connected to the first surface of the first gel elastomer sheet. A first film is releasably connected to the first adhesive layer. A second gel elastomer sheet including a third surface and a fourth surface is provided, and the fourth surface of the second gel elastomer sheet is releasably connectable to the second surface of the first gel elastomer sheet. A second adhesive layer is releasably connected to the third surface of the second gel elastomer sheet, and a second film is releasably connected to the second adhesive layer.

A releasable band is provided. The releasable band includes an elongated pliable material strip including a first end and a second end. A first elastomer gel piece is connected to the first end of the elongated pliable material strip. A second elastomer gel piece is connected to the second end of the elongated pliable material strip. The second elastomer gel piece is releasably connectable to the first elastomer gel piece.

A method for connecting a user to a platform is provided. The method includes providing a band. The band includes an elongated pliable material strip including a first end and a second end, a first elastomer gel piece connected to the first end of the elongated pliable material strip, and a second elastomer gel piece connected to the second end of the elongated pliable material strip. A platform is provided, and the user is positioned on the platform. The band is wrapped around the platform and the user, and the second elastomer gel piece is releasably connected to the first elastomer gel piece.

BRIEF DESCRIPTION OF THE DRAWING(S)

A more detailed understanding may be had from the following description, given by way of example with the accompanying drawings. The Figures in the drawings and the detailed description are examples. The Figures and the detailed description are not to be considered limiting and other examples are possible. Like reference numerals in the Figures indicate like elements wherein:

FIG. 14 is an exploded perspective view of another user examination table assembly.

FIGS. 20A, 20B, 21A, 21B are side elevation views of still other user positioning setups including user positioning devices of FIGS. 2A-2D and 3A-3D and the releasable band of FIG. 16A.

FIG. 22 is a diagram showing a method for connecting a user to a platform.

FIG. 23 is a diagram showing a user positioning method.

DETAILED DESCRIPTION OF ILLUSTRATIVE EMBODIMENT(S)

Figure 1A:
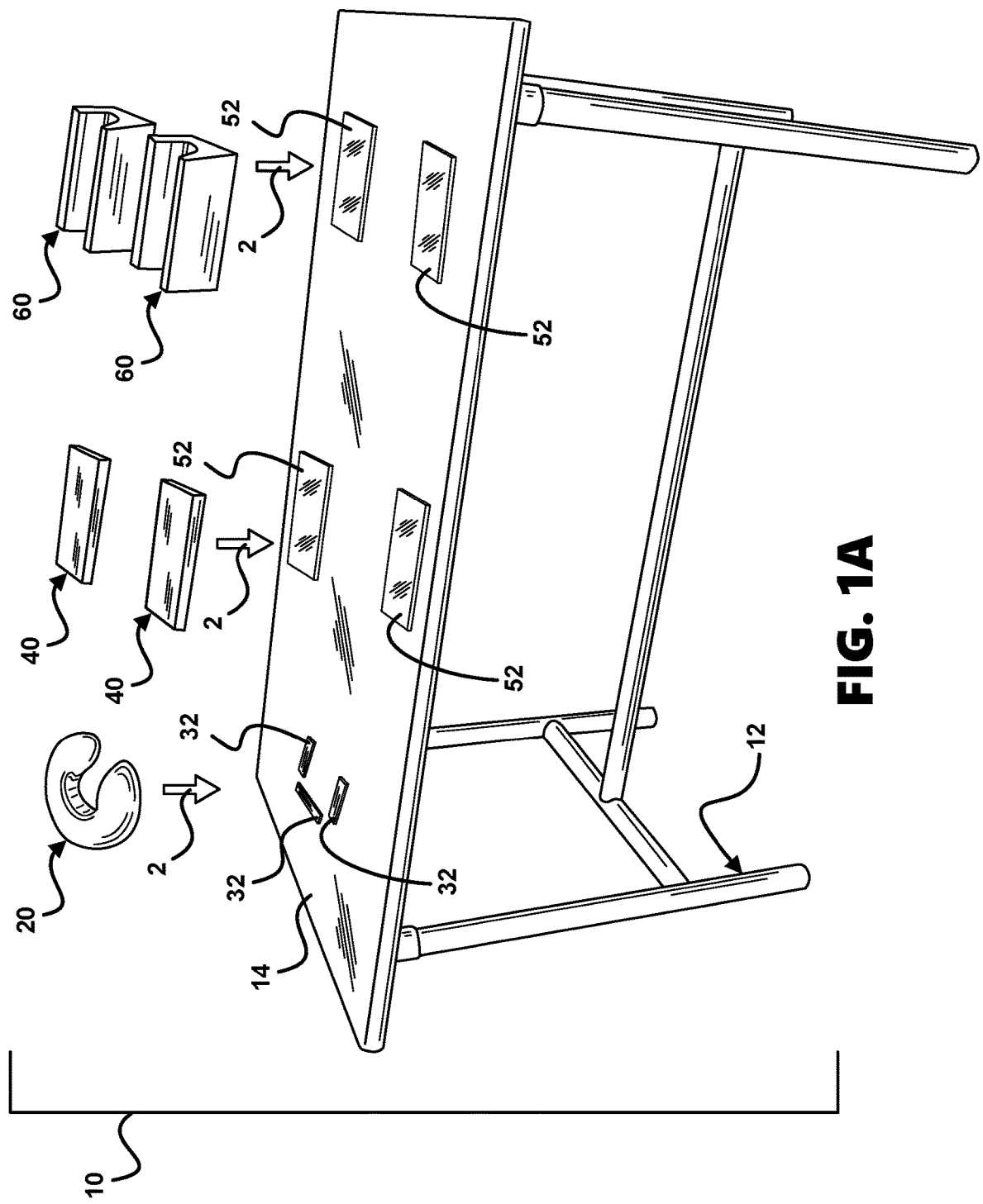
FIG. 1A is an exploded perspective view of a user examination table assembly.

Certain terminology is used in the following description for convenience only and is not limiting. The words "right," "left," "top," and "bottom" designate directions in the drawings to which reference is made. The words "a" and "one" are defined as including one or more of the referenced item unless specifically stated otherwise. This terminology includes the words above specifically mentioned, derivatives thereof, and words of similar import. The phrase "at least one" followed by a list of two or more items, such as A, B, or C, means any individual one of A, B or C as well as any combination thereof.

Figure 1B:
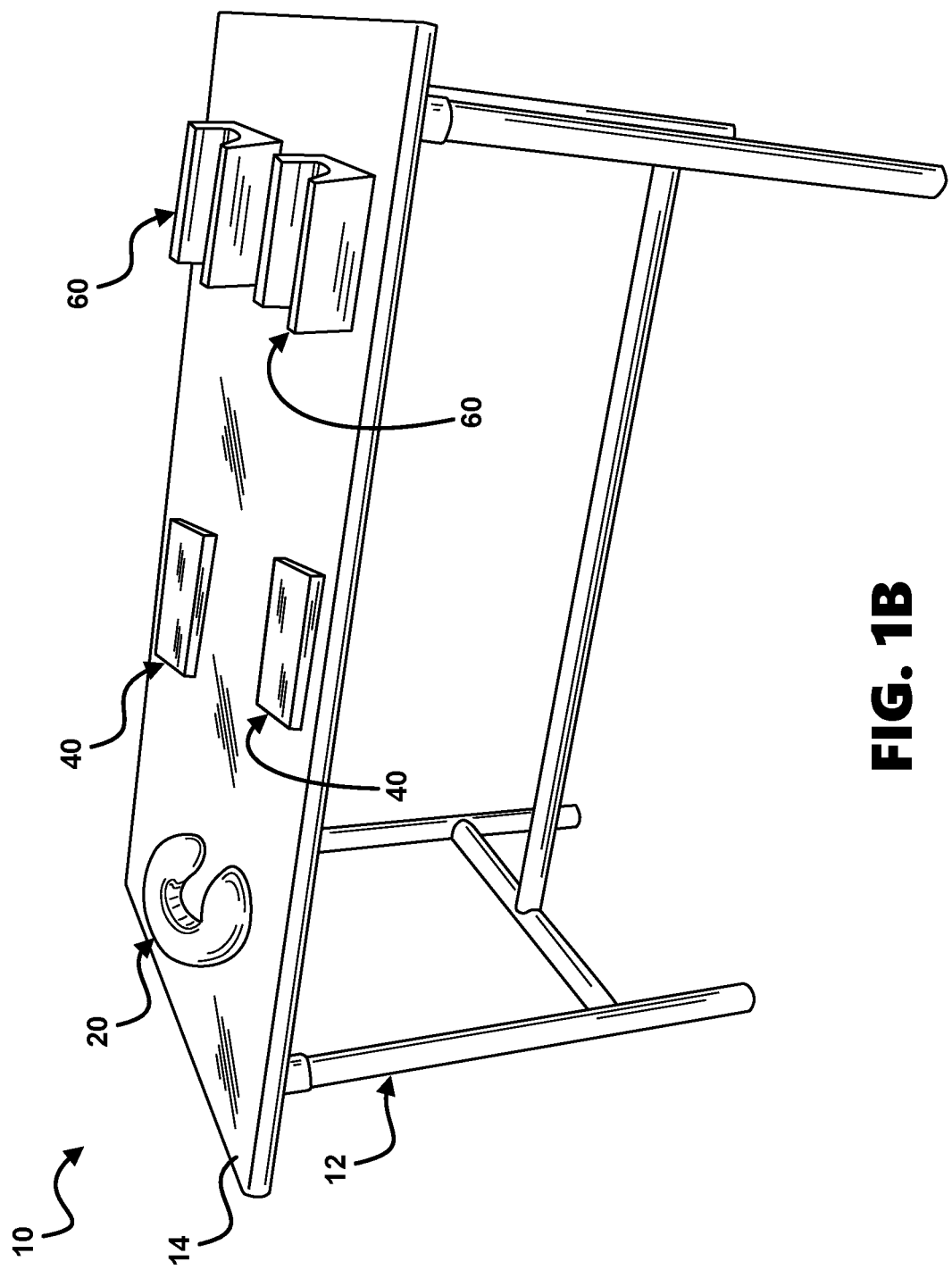
FIG. 1B is an assembled perspective view of the user examination table assembly of FIG. 1A.
Figure 2A:
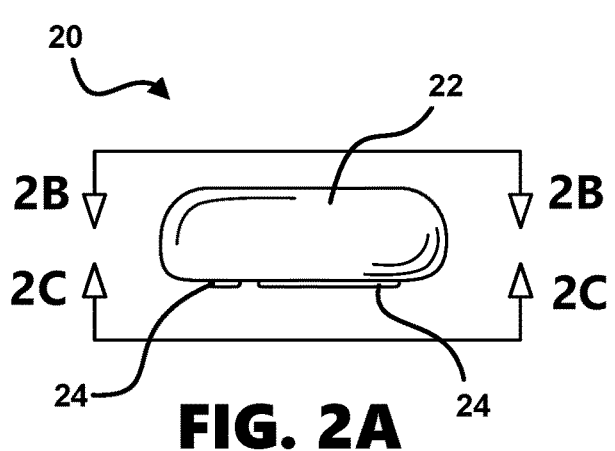
FIG. 2A is a side elevation view of a user positioning device.
Figure 2B:
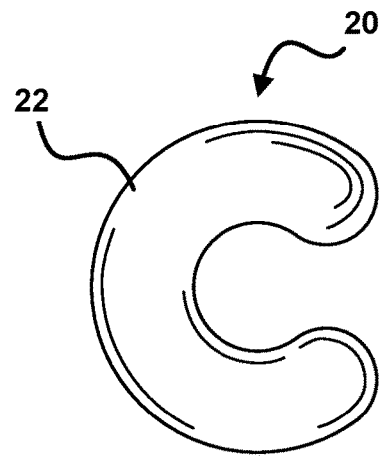
FIG. 2B is a top plan view of the user positioning device of FIG. 2A taken along line 2B-2B of FIG. 2A.
Figure 2D:
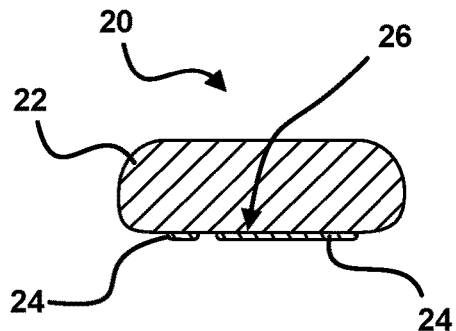
FIG. 2D is a cross-section view of the user positioning device of FIG. 2A taken along line 2D-2D of FIG. 2C.
Figure 2C:
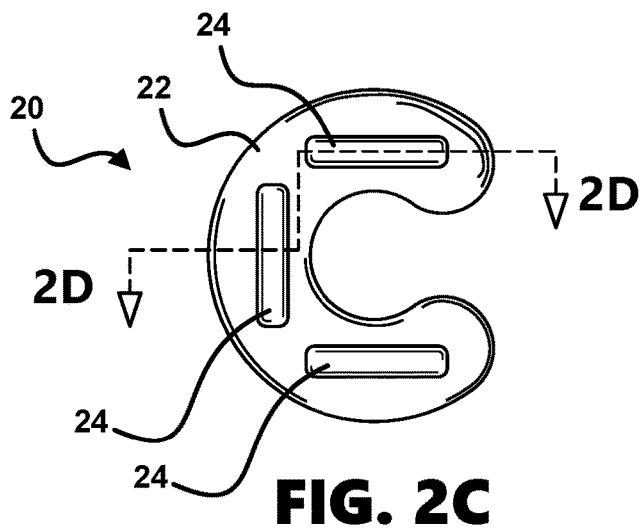
FIG. 2C is a bottom plan view of the user positioning device of FIG. 2A taken along line 2C-2C of FIG. 2A.
Figure 3A:
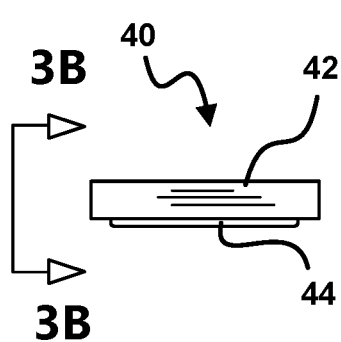
FIG. 3A is a front elevation view of another user positioning device.
Figure 3B:
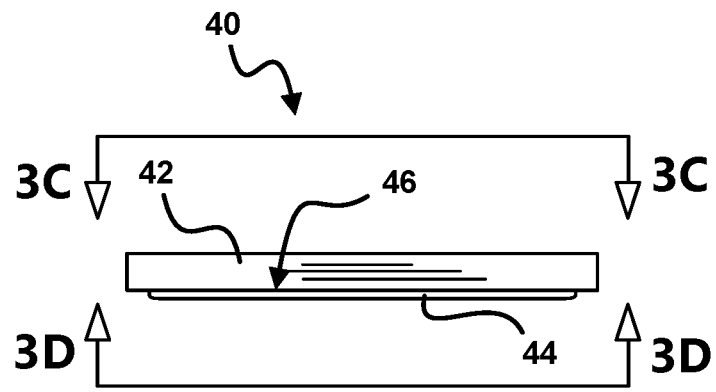
FIG. 3B is a side elevation view of the user positioning device of FIG. 3A taken along line 3B-3B of FIG. 3A.
Figure 3C:
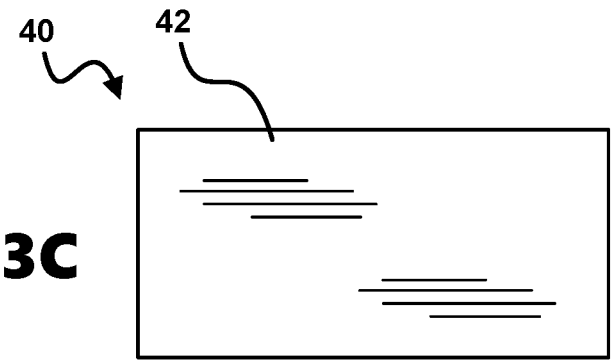
FIG. 3C is a top plan view of the user positioning device of FIG. 3A taken along line 3C-3C of FIG. 3B.
Figure 3D:
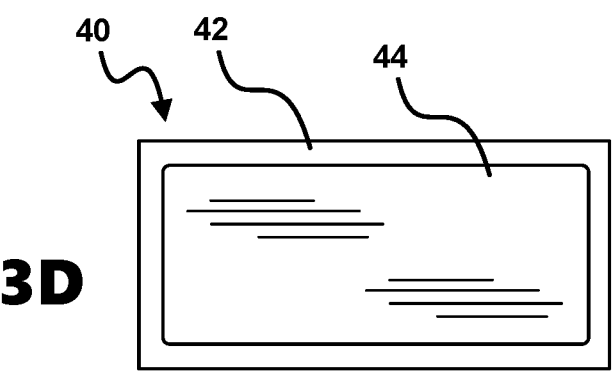
FIG. 3D is a bottom plan view of the user positioning device of FIG. 3A taken along line 3D-3D of FIG. 3B.
Figure 4A:
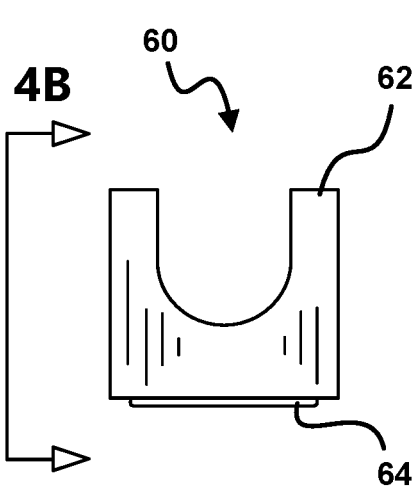
FIG. 4A is a front elevation view of yet another user positioning device.
Figure 4B:
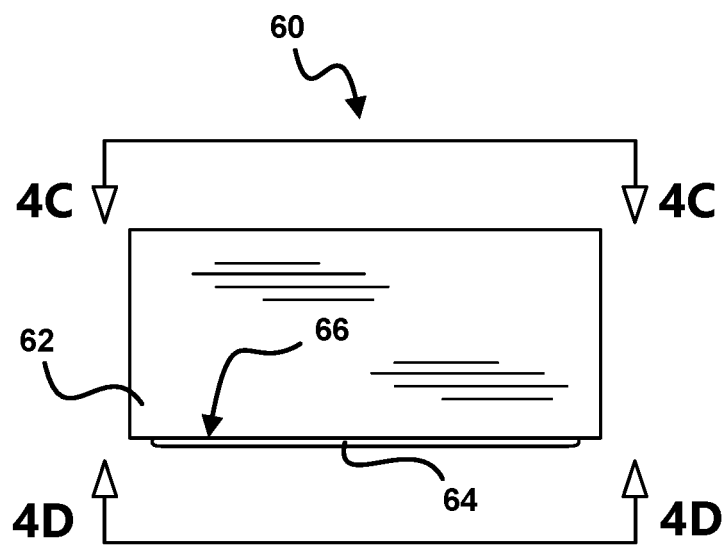
FIG. 4B is a side elevation view of the user positioning device of FIG. 4A taken along line 4B-4B of FIG. 4A.
Figure 4C:
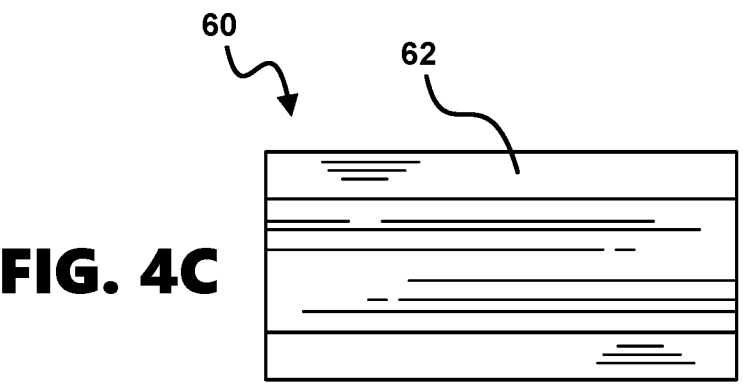
FIG. 4C is a top plan view of the user positioning device of FIG. 4A taken along line 4C-4C of FIG. 4B.
Figure 4D:
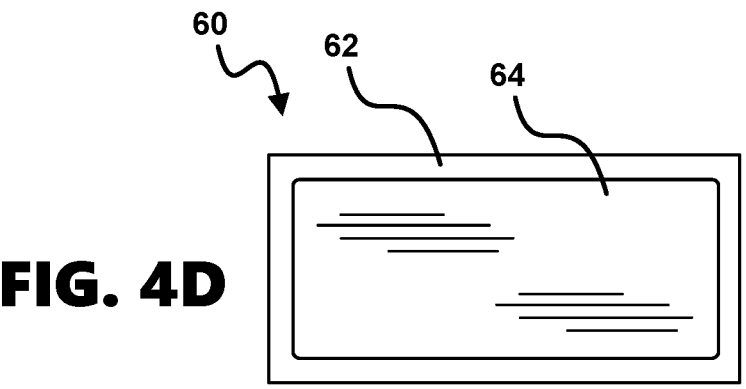
FIG. 4D is a bottom plan view of the user positioning device of FIG. 4A taken along line 4D-4D of FIG. 4B.
Figure 5A:
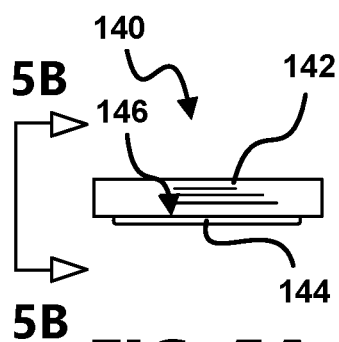
FIG. 5A is a front elevation view of still another user positioning device.
Figure 5B:
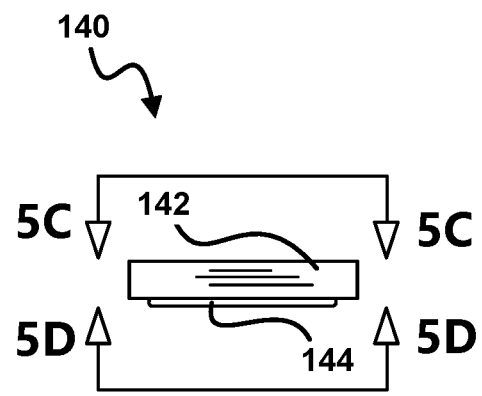
FIG. 5B is a side elevation view of the user positioning device of FIG. 5A taken along line 5B-5B of FIG. 5A.
Figure 5C:
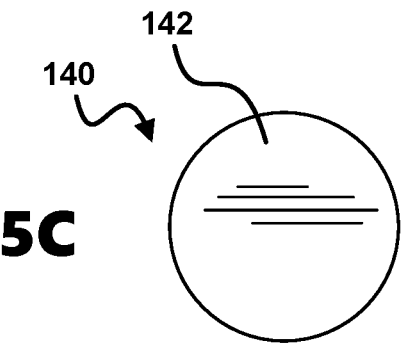
FIG. 5C is a top plan view of the user positioning device of FIG. 5A taken along line 5C-5C of FIG. 5B.
Figure 5D:
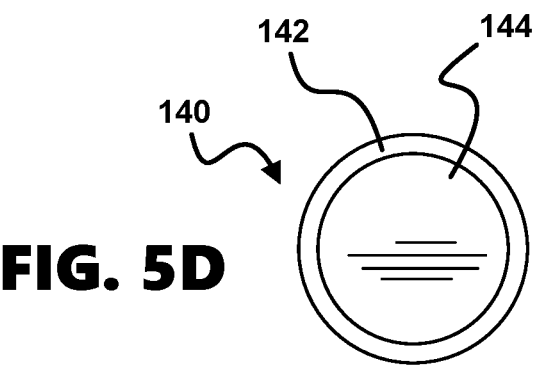
FIG. 5D is a bottom plan view of the user positioning device of FIG. 5A taken along line 5D-5D of FIG. 5B.
Figure 6A:
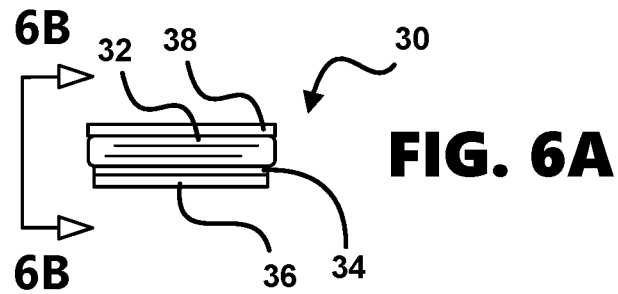
FIG. 6A is a front elevation view of a gel elastomer assembly.
Figure 6B:
FIG. 6B is a side elevation view of the gel elastomer assembly of FIG. 6A taken along line 6B-6B of FIG. 6A.
Figure 6C:
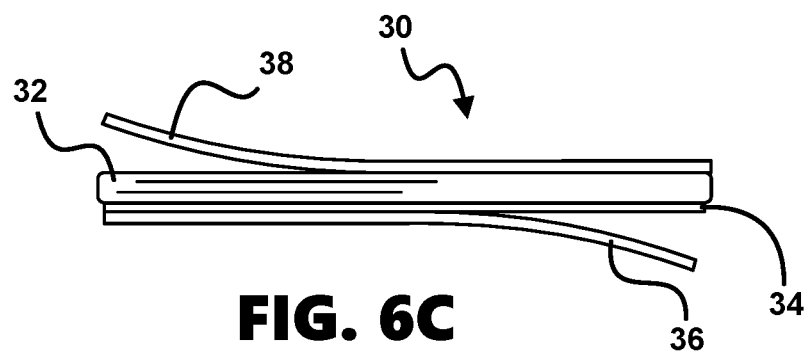
FIG. 6C is a side elevation view of the gel elastomer assembly of FIG. 6A depicting the partial removal of an adhesive backing film and a protective liner film.
Figure 6D:
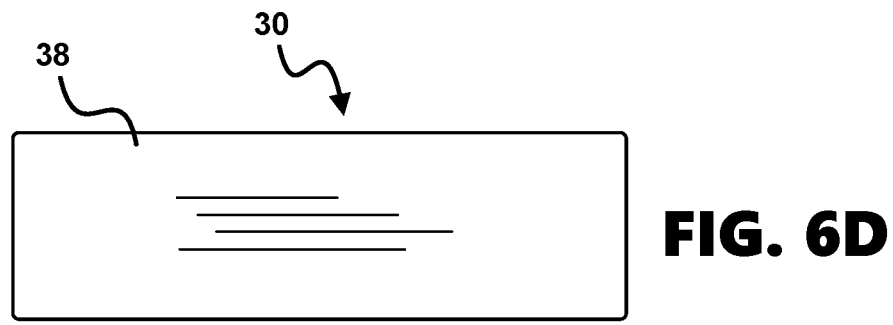
FIG. 6D is a top plan view of the gel elastomer assembly of FIG. 6A taken along line 6D-6D of FIG. 6B.
Figure 6E:
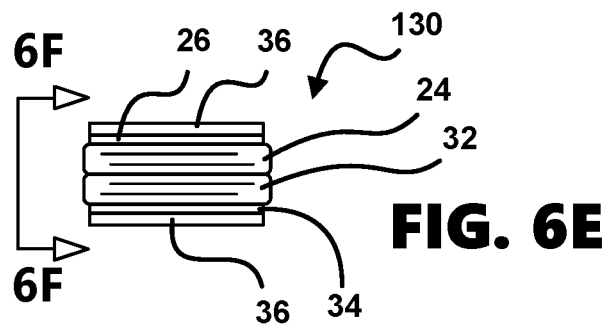
FIG. 6E is a front elevation view of another gel elastomer assembly.
Figure 6F:
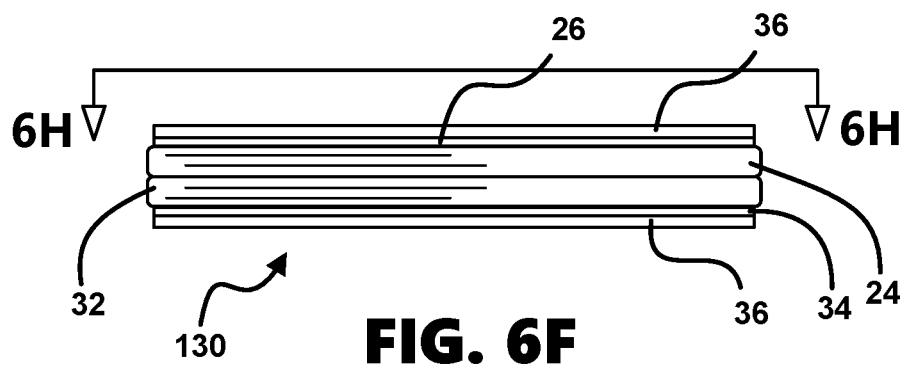
FIG. 6F is a side elevation view of the gel elastomer assembly of FIG. 6E taken along line 6F-6F of FIG. 6E.
Figure 6G:
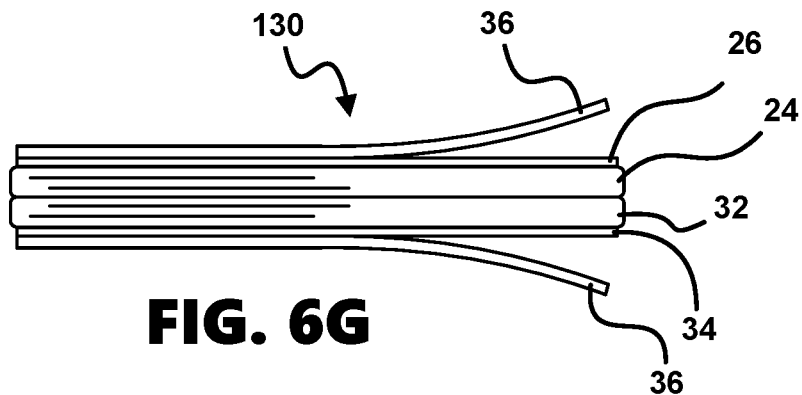
FIG. 6G is a side elevation view of the gel elastomer assembly of FIG. 6E depicting the partial removal of adhesive backing films.
Figure 6H:
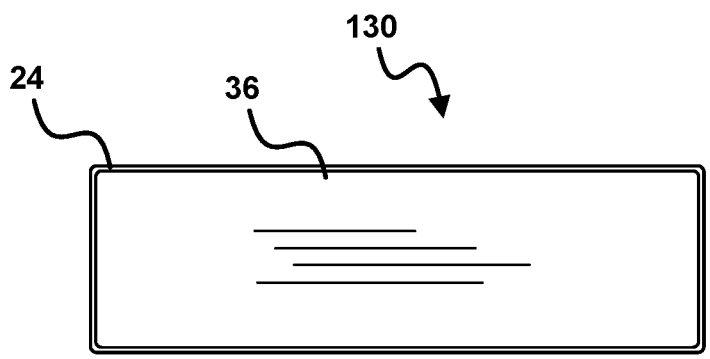
FIG. 6H is a top plan view of the gel elastomer assembly of FIG. 6E taken along line 6H-6H of FIG. 6F.
Figure 7A:
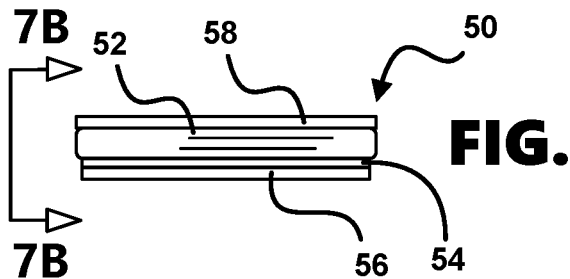
FIG. 7A is a front elevation view of yet another gel elastomer assembly.
Figure 7B:
FIG. 7B is a side elevation view of the gel elastomer assembly of FIG. 7A taken along line 7B-7B of FIG. 7A.
Figure 7C:
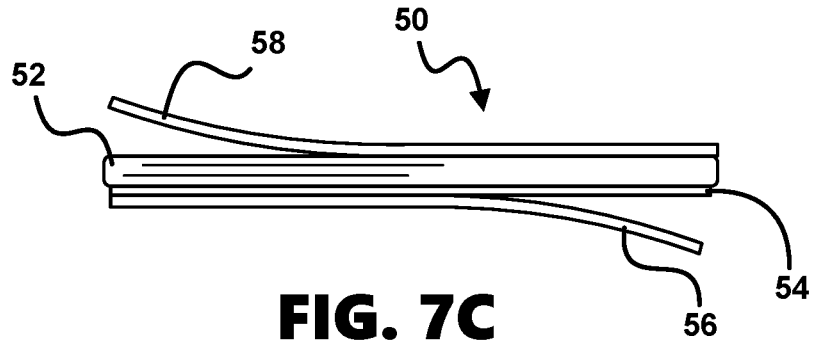
FIG. 7C is a side elevation view of the gel elastomer assembly of FIG. 7A depicting the partial removal of an adhesive backing film and a protective liner film.
Figure 7D:
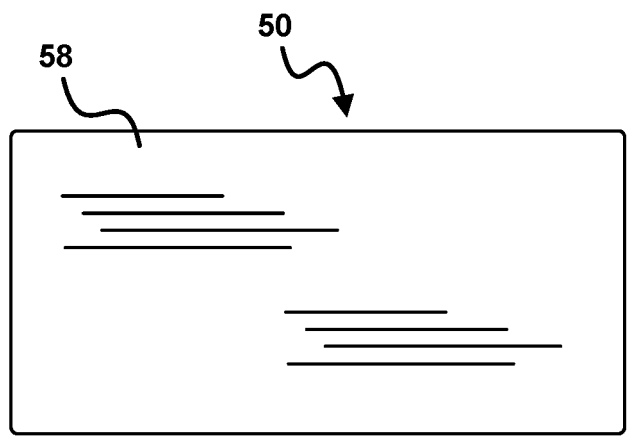
FIG. 7D is a top plan view of the gel elastomer assembly of FIG. 7A taken along line 7D-7D of FIG. 7B.
Figure 8A:
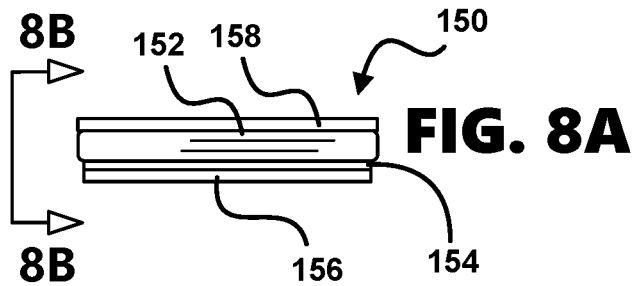
FIG. 8A is a front elevation view of yet another gel elastomer assembly.
Figure 8B:
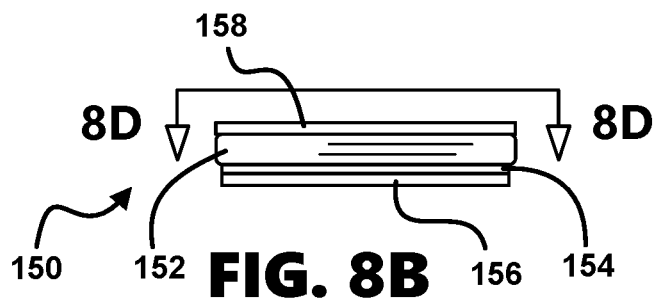
FIG. 8B is a side elevation view of the gel elastomer assembly of FIG. 8A taken along line 8B-8B of FIG. 8A.
Figure 8C:
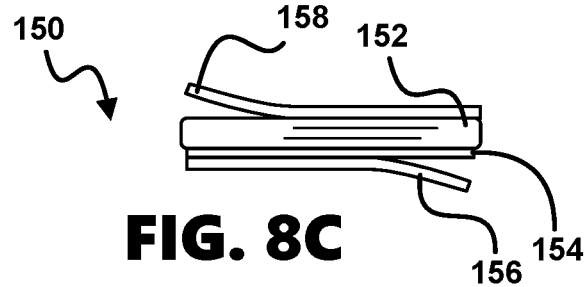
FIG. 8C is a side elevation view of the gel elastomer assembly of FIG. 8A depicting the partial removal of an adhesive backing film and a protective liner film.
Figure 8D:
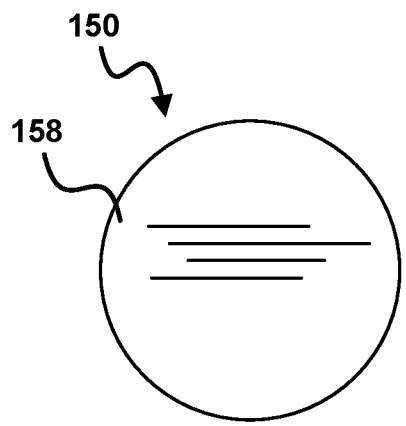
FIG. 8D is a top plan view of the gel elastomer assembly of FIG. 8A taken along line 8D-8D of FIG. 8B.

Referring to FIGS. 1A and 1B, a first user examination table assembly 10 is shown including user positioning devices 20, 40, 60 releasably connectable to a tabletop 14 of an examination table 12, as shown by arrows 2, for example for use in securing or positioning a patient during medical or palliative treatments or procedures. The tabletop 14 can include one or more of a metallic material, hard or soft polymeric material, finished wood material, or smooth upholstered textile material (e.g., a vinyl textile). A first user positioning device in the form of a U-shaped positioning device 20, a second user positioning device in the form of a rectangular prism shaped positioning device 40, and a third user positioning device in the form of a channel shaped positioning device 60 are provided to be releasably connectable to the tabletop 14 or other surface.

Referring to FIGS. 2A-2D, 3A-3D, and 4A-4D, the U-shaped positioning device 20 includes a U-shaped positioning pad 22, the rectangular prism shaped positioning device 40 includes a rectangular prism shaped positioning pad 42, and the channel shaped positioning device 60 includes a channel shaped positioning pad 62. Referring further to FIGS. 5A-5D, a fourth user positioning device in the form of a circular prism shaped positioning device 140 including a circular prism shaped positioning pad 142 can also be releasably connected to the tabletop 14 or other surface.

The positioning pads 22, 42, 62, 142 are malleable and preferably formed of a foam, for example a polyurethane foam form or silicone foam form, having a durometer in the Shore OO range. A first gel elastomer sheet 24 is attached at three locations to the U-shaped positioning pad 22 by a first adhesive layer 26. A second gel elastomer sheet 44 is attached to the rectangular prism shaped positioning pad 42 by a second adhesive layer 46. A third gel elastomer sheet 64 is attached to the channel shaped positioning pad 62 by a third adhesive layer 66. A fourth gel elastomer sheet 144 is attached to the circular prism shaped positioning pad 142 by a fourth adhesive layer 146. Alternatively, the first, second, third, and fourth gel elastomer sheets 24, 44, 64, 144 can respectively be integrally formed with the U-shaped positioning pad 22, rectangular prism shaped positioning pad 42, channel shaped positioning pad 62, and circular prism shaped positioning pad 142, and each positioning pad 22, 42, 62, 142 can also be formed of a gel elastomer. The first, second, third, and fourth gel elastomer sheets 24, 44, 64, 144 enable a releasable bond for respectively securing the positioning pads 22, 42, 62, 142 to a surface, for example the tabletop 14.

Referring to FIGS. 6A-6D, 7A-7D, and 8A-8D, a fifth gel elastomer sheet 32, sixth gel elastomer sheet 52, and seventh gel elastomer sheet 152 are preferably provided to users respectively as a first gel elastomer assembly 30, a second gel elastomer assembly 50, and a third gel elastomer assembly 150 with a respective fifth adhesive layer 34, sixth adhesive layer 54, and seventh adhesive layer 154, with a respective first releasable adhesive backing film 36, second releasable adhesive backing film 56, and third releasable adhesive backing film 156, and with a respective first releasable protective liner film 38, second releasable protective liner film 58, and third releasable protective liner film 158. A user can remove one or more of the releasable adhesive backing films 36, 56, 156 and attach one or more of the fifth, sixth, and seventh gel elastomer sheets 32, 52, 152 to a surface via the respective fifth, sixth, and seventh adhesive layers 34, 54, 154, for example to the tabletop 14, and remove the respective releasable protective liner films 38, 58, 158 to expose the respective fifth, sixth, and seventh gel elastomer sheets 32, 52, 152. The releasable protective liner films 38, 58, 158 respectively protect the fifth, sixth, and seventh gel elastomer sheets 32, 52, 152 from collecting dust and other contaminants when the fifth, sixth, and seventh gel elastomer sheets 32, 52, 152 are not in use, which releasable protective liner films 38, 58, 158 can be removed and replaced for reuse as needed. The first releasable protective liner film 38 can also be used over the first gel elastomer sheet 24, the second releasable protective liner film 58 can also be used over the second gel elastomer sheet 44 and the third gel elastomer sheet 64, and the third releasable protective liner film 158 can also be used over the fourth gel elastomer sheet 144, which releasable protective liner films 38, 58, 158 can be removed to expose the respective first, second, third, and fourth gel elastomer sheets 24, 44, 64, 144 for use and later returned to protect the respective first, second, third, and fourth gel elastomer sheets 24, 44, 64, 144 from dust and other contaminants when not in use.

Referring to FIGS. 6E-6H, a fourth gel elastomer assembly 130 includes the first gel elastomer sheet 24 and the fifth gel elastomer sheet 32 releasably connected together. The first gel elastomer sheet 24 is provided with the first adhesive layer 26, and the fifth gel elastomer sheet 32 is provided with the fifth adhesive layer 34. One of the first adhesive backing films 36 is releasably attached to the first adhesive layer 26, and another first adhesive backing film 36 is releasably attached to the fifth adhesive layer 34. Using the fourth gel elastomer assembly 130, a user is enabled to remove the first adhesive backing films 36 to connect the first gel elastomer sheet 24 and the fifth gel elastomer sheet 32 to opposing surfaces, for example to surfaces of the U-shaped positioning pad 22 and the tabletop 14, respectively via the first adhesive layer 26 and the fifth adhesive layer 34 thereby connecting the opposing surfaces. Thereafter, the opposing surfaces can be disconnected by separating the first gel elastomer sheet 24 from the fifth gel elastomer sheet 32.

The first, second, third, and fourth adhesive layers 26, 46, 66, 146 preferably include acrylic permanent high tack pressure sensitive adhesive ("PSA") or semi-permanent high tack pressure sensitive adhesive. The fifth, sixth, and seventh adhesive layers 34, 54, 154 also preferably include acrylic permanent or semi-permanent high tack pressure sensitive adhesive. The adhesive of the first, second, third, and fourth adhesive layers 26, 46, 66, 146 can be the same as the adhesive of the fifth, sixth, and seventh adhesive layers 34, 54, 154. Alternatively, the adhesive of the fifth, sixth, and seventh adhesive layers 34, 54, 154 can be less strong (i.e., lower tack) than the adhesive of the first, second, third, and fourth adhesive layers 26, 46, 66, 146 to facilitate removal of the fifth, sixth, and seventh gel elastomer sheets 32, 52, 152 from surfaces onto which they are attached.

Figure 9A:
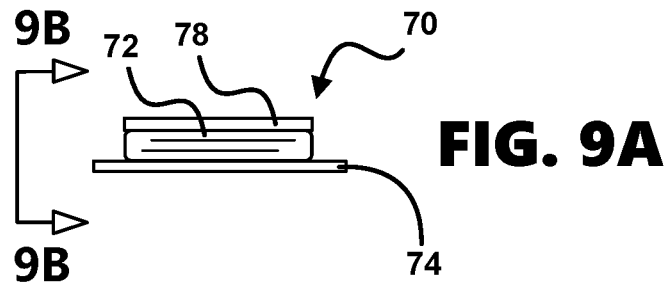
FIG. 9A is a front elevation view of still another gel elastomer assembly.
Figure 9B:
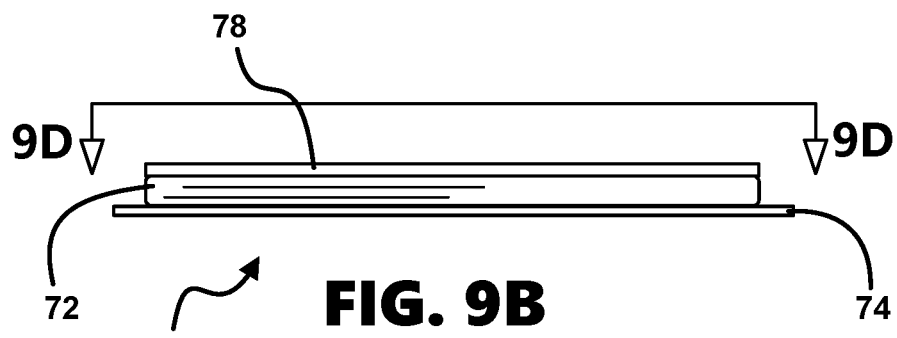
FIG. 9B is a side elevation view of the gel elastomer assembly of FIG. 9A taken along line 9B-9B of FIG. 9A.
Figure 9C:
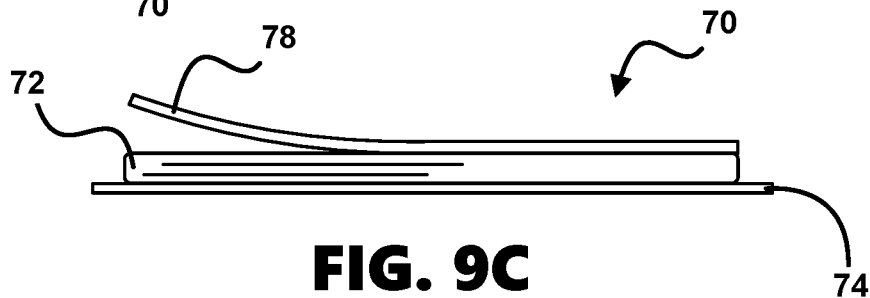
FIG. 9C is a side elevation view of the gel elastomer assembly of FIG. 9A depicting the partial removal of a protective liner film.
Figure 9D:
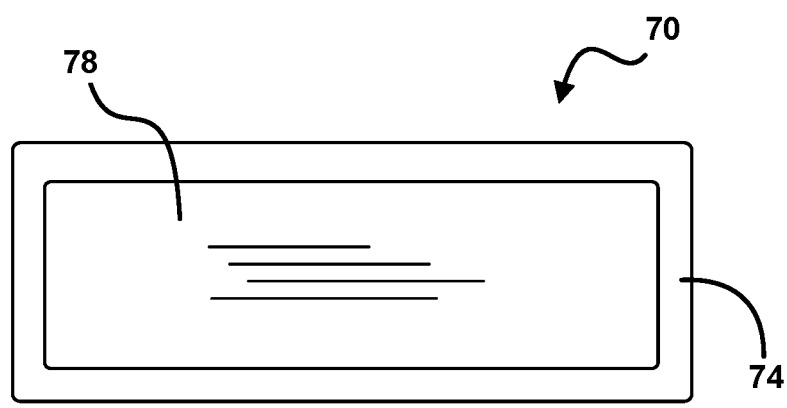
FIG. 9D is a top plan view of the gel elastomer assembly of FIG. 9A taken along line 9D-9D of FIG. 9B.
Figure 10A:
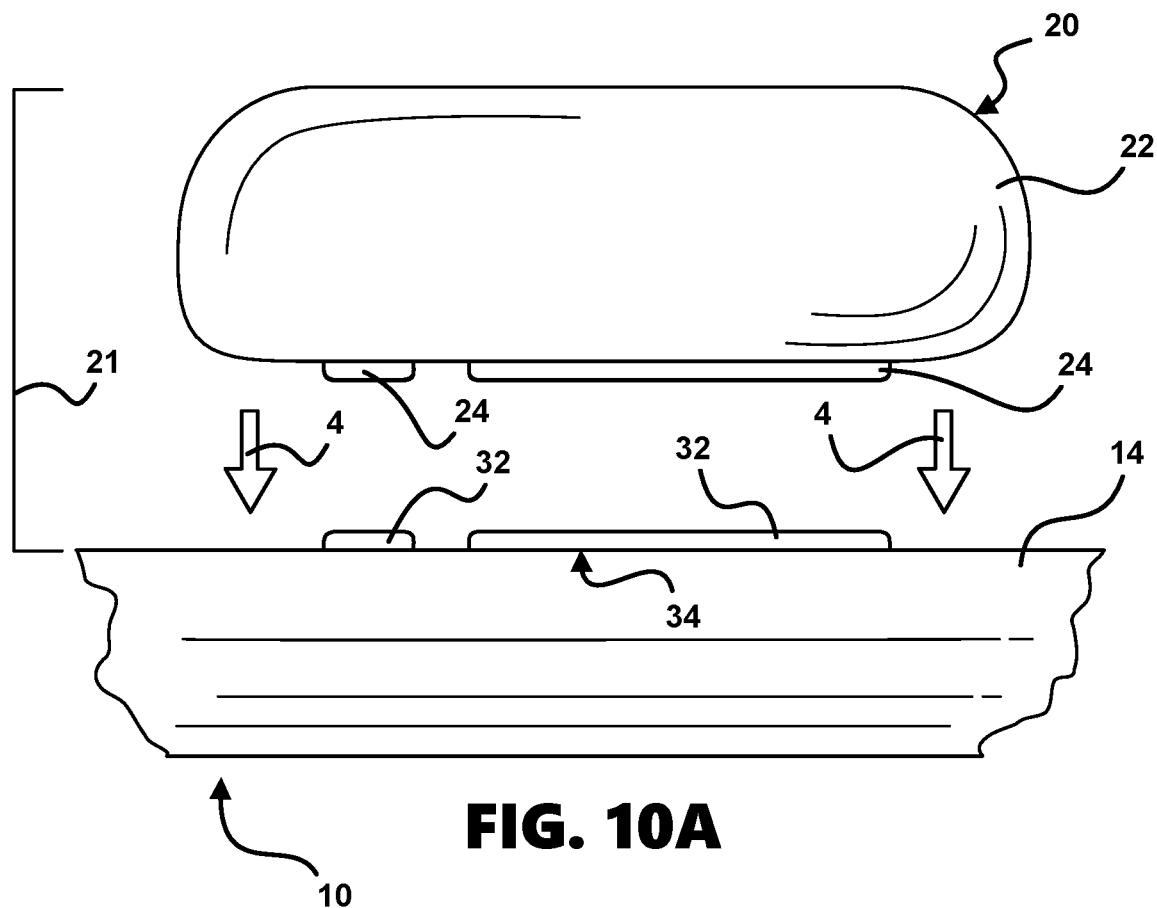
FIGS. 10A and 10B are respective exploded and assembled side elevation detail views of the user examination table assembly of FIGS. 1A and 1B showing a U-shaped positioning device.
Figure 10B:
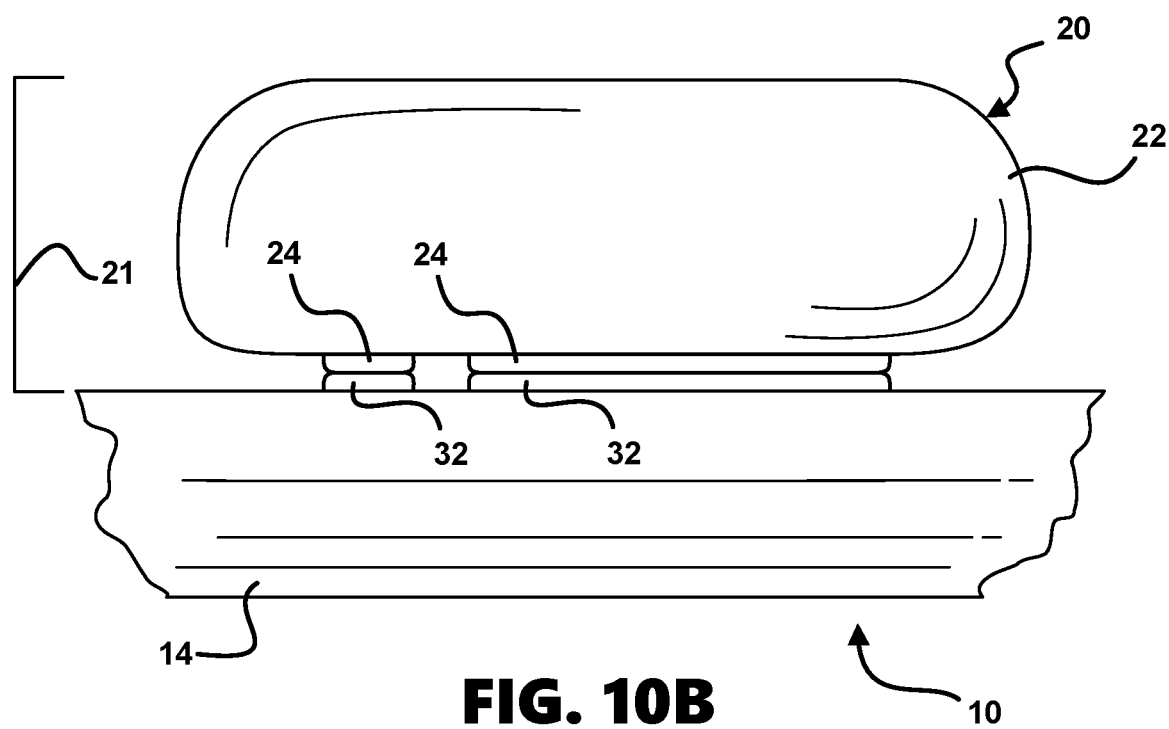
Figure 11A:
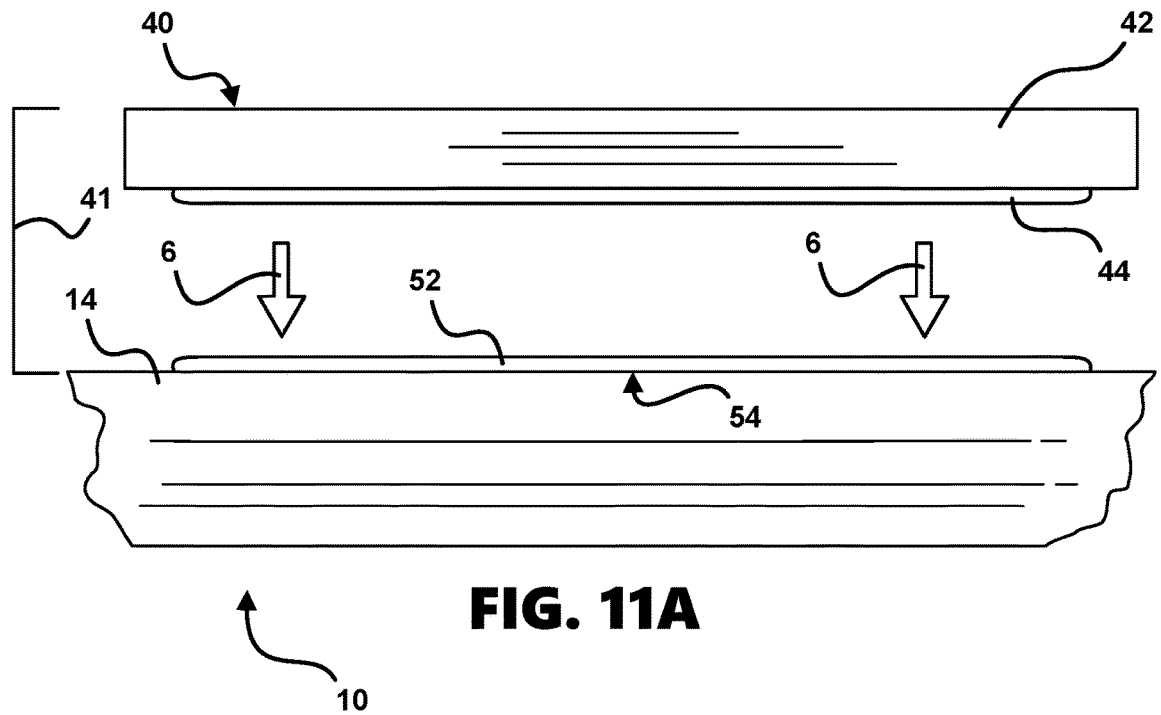
FIGS. 11A and 11B are respective exploded and assembled side elevation detail views of the user examination table assembly of FIGS. 1A and 1B showing a rectangular prism shaped positioning device.
Figure 11B:
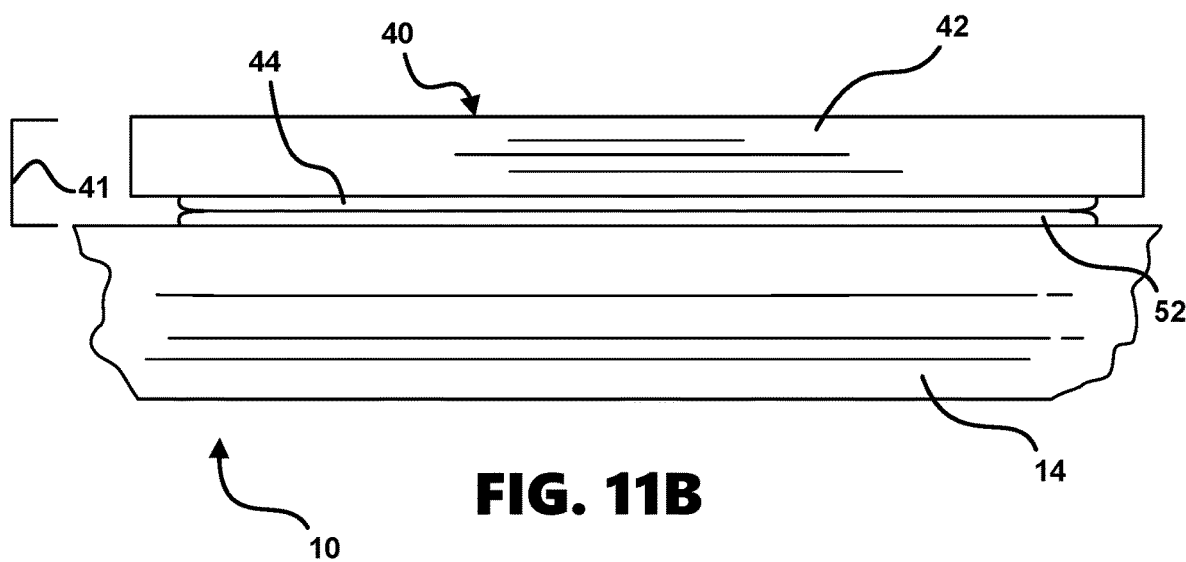
Figure 12A:
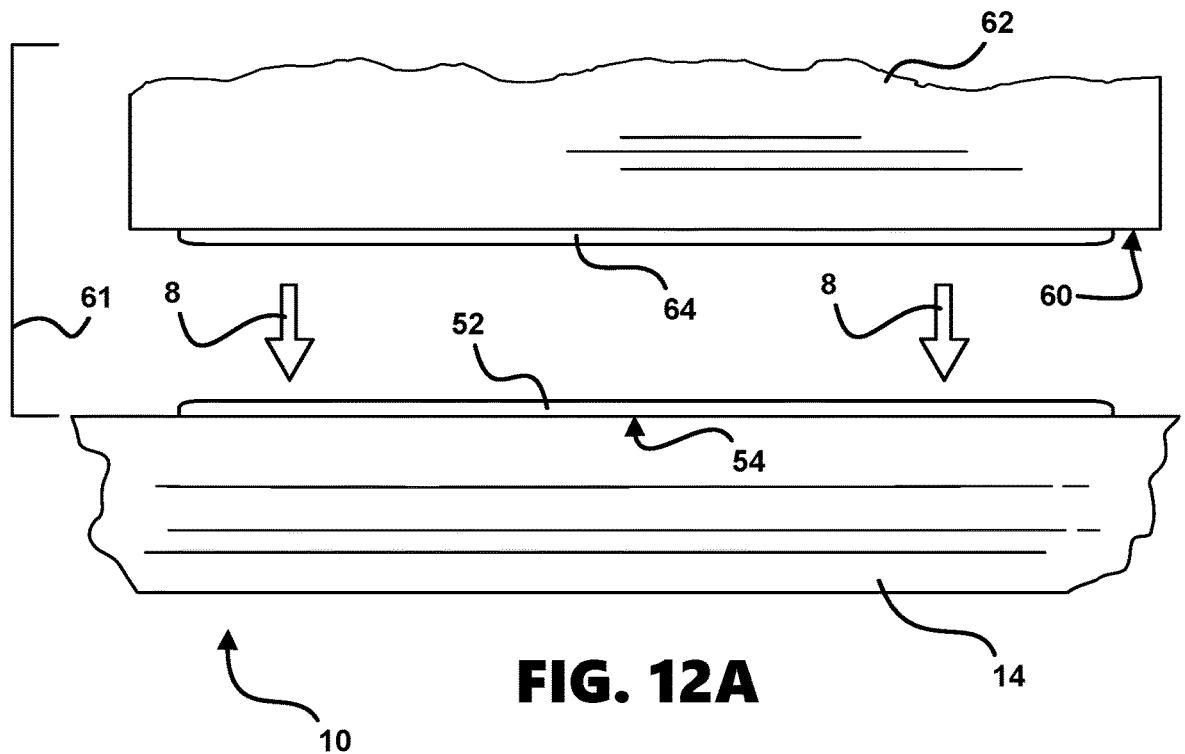
FIGS. 12A and 12B are respective exploded and assembled side elevation detail views of the user examination table assembly of FIGS. 1A and 1B showing a channel shaped positioning device.
Figure 12B:
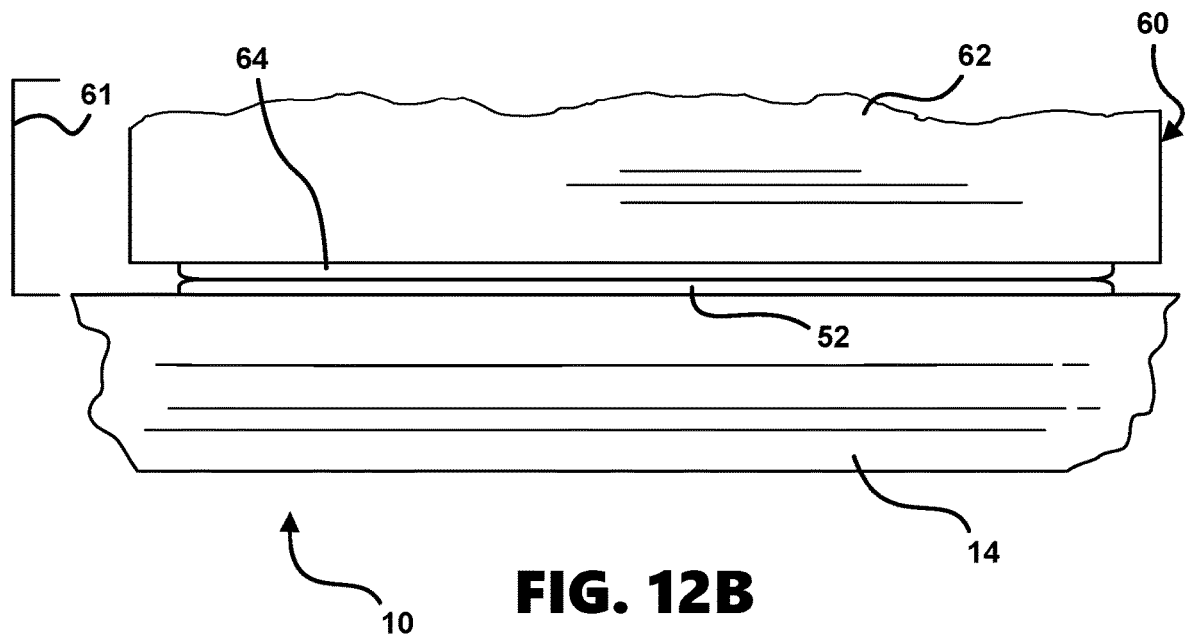

Referring to FIG. 9A, a fifth gel elastomer assembly 70 includes an eighth gel elastomer sheet 72 and a pliable material sheet 74 attached to the eighth gel elastomer sheet 72. The eighth gel elastomer sheet 72 and the pliable material sheet 74 are preferably cast together during a curing process of the eighth gel elastomer sheet 72. A fourth releasable protective liner film 78 is provided to protect the eighth gel elastomer sheet 72 from collecting dust and other contaminants when not in use. The fifth gel elastomer assembly 70 can be attached to positioning devices, for example the positioning pads 22, 42, 62, 142 by sewing through the pliable material sheet 74, or alternatively by connecting the pliable material sheet via other mechanical or chemical attachment methods.

Referring to FIGS. 10A, 10B, 11A, 11B, 12A, and 12B, details of attaching the user positioning devices 20, 40, 60 to the tabletop 14 are shown. The fifth gel elastomer sheet 32 is adhered to the tabletop 14 by the fifth adhesive layer 34, and the U-shaped positioning device 20 is releasably connected to the fifth gel elastomer sheet 32 by the first gel elastomer sheet 24 as shown by the arrows 4 to releasably secure the U-shaped positioning device 20 to the tabletop 14. The U-shaped positioning device 20 is releasably connectable to the fifth gel elastomer sheet 32 to form a first positioning apparatus 21 that can alternatively be attached via the fifth adhesive layer 34 to a multitude of surfaces other than the tabletop 14.

The sixth gel elastomer sheet 52 is adhered to the tabletop 14 by the sixth adhesive layer 54, and the rectangular prism shaped positioning device 40 is releasably connected to the sixth gel elastomer sheet 52 by the second gel elastomer sheet 44 as shown by the arrows 6 to releasably secure the rectangular prism shaped positioning device 40 to the tabletop 14. The rectangular prism shaped positioning device 40 is releasably connectable to the sixth gel elastomer sheet 52 to form a second positioning apparatus 41 that can alternatively be attached via the sixth adhesive layer 54 to a multitude of surfaces other than the tabletop 14.

Another sixth gel elastomer sheet 52 is adhered to the tabletop 14 by the sixth adhesive layer 54, and the channel shaped positioning device 60 is releasably connected to the sixth gel elastomer sheet 52 by the third gel elastomer sheet 64 as shown by the arrows 8 to releasably secure the channel shaped positioning device 60 to the tabletop 14. The channel shaped positioning device 60 is releasably connectable to the sixth gel elastomer sheet 52 to form a third positioning apparatus 61 that can alternatively be attached via the sixth adhesive layer 54 to a multitude of surfaces other than the tabletop 14.

Figure 13A:
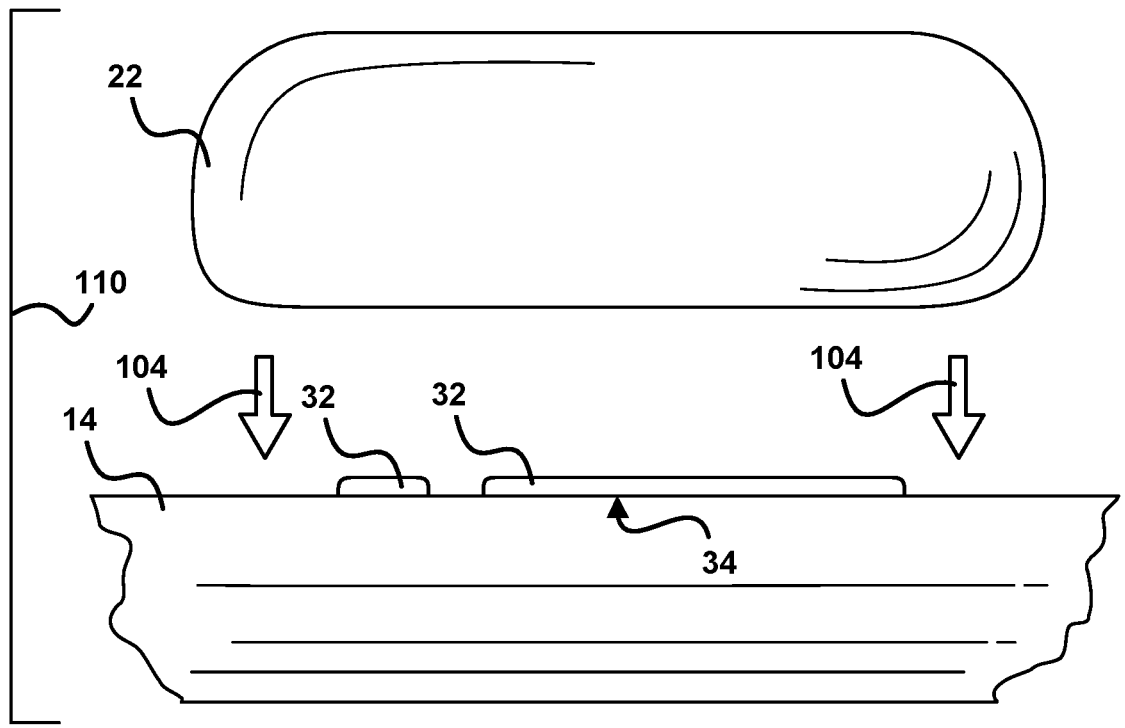
FIGS. 13A and 13B are respective exploded and assembled side elevation detail views of another user examination table assembly.
Figure 13B:
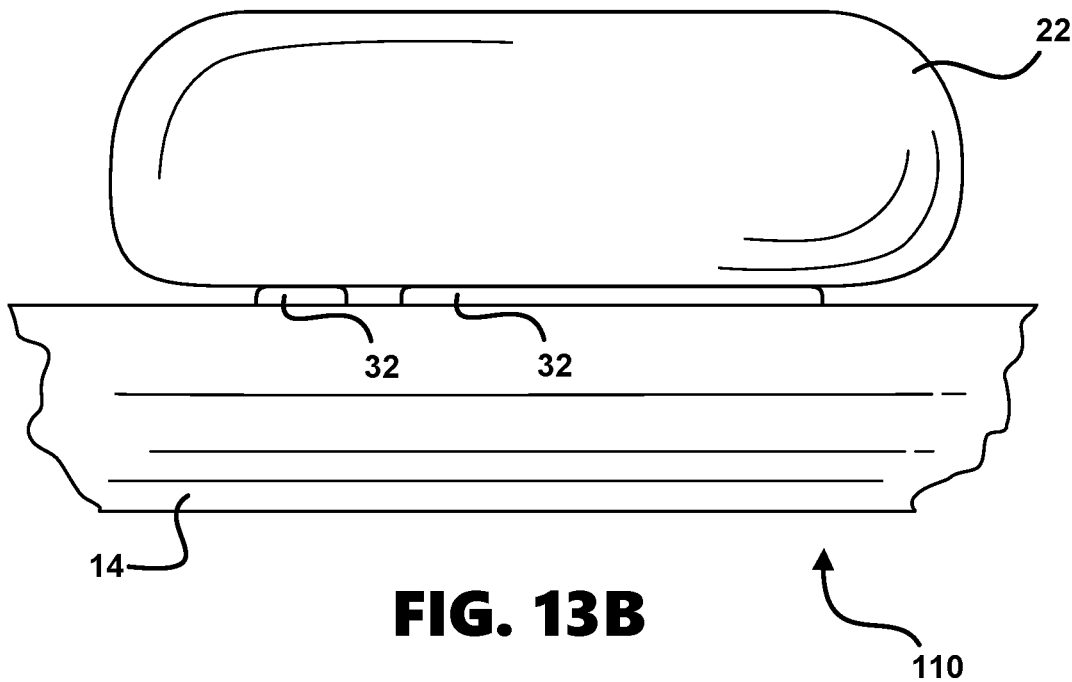

Referring to FIGS. 13A and 13B, a portion of a second user examination table assembly 110 is shown in which the U-shaped positioning pad 22 is provided without the first gel elastomer sheet 24 and without the first adhesive layer 26. The fifth gel elastomer sheet 32 is adhered to the tabletop 14 by the fifth adhesive layer 34. The U-shaped positioning pad 22 as shown by arrows 104 is releasably attached directly to the fifth gel elastomer sheet 32. The fifth gel elastomer sheet 32 provides suitable tackiness to enable adhesion to the U-shaped positioning pad 22 which preferably has a smooth surface to facilitate adhesion.

Figure 15A:
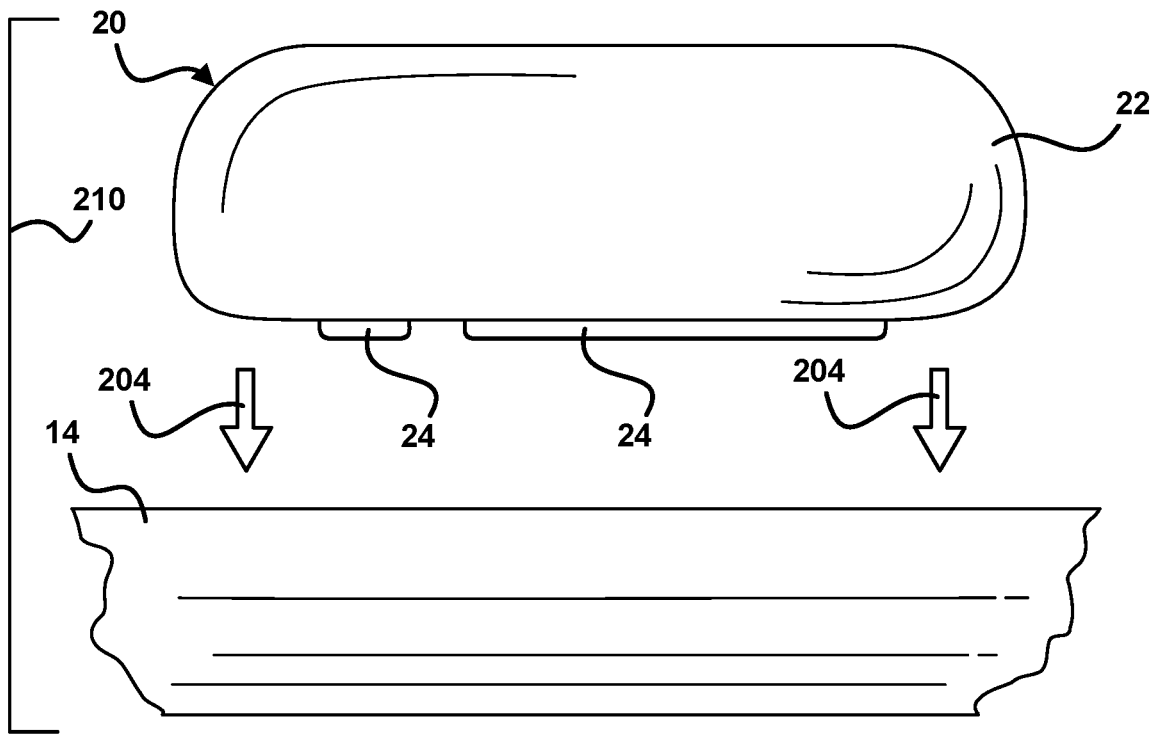
FIGS. 15A and 15B are respective exploded and assembled side elevation detail views of the user examination table assembly of FIG. 14 showing a U-shaped positioning device.
Figure 15B:
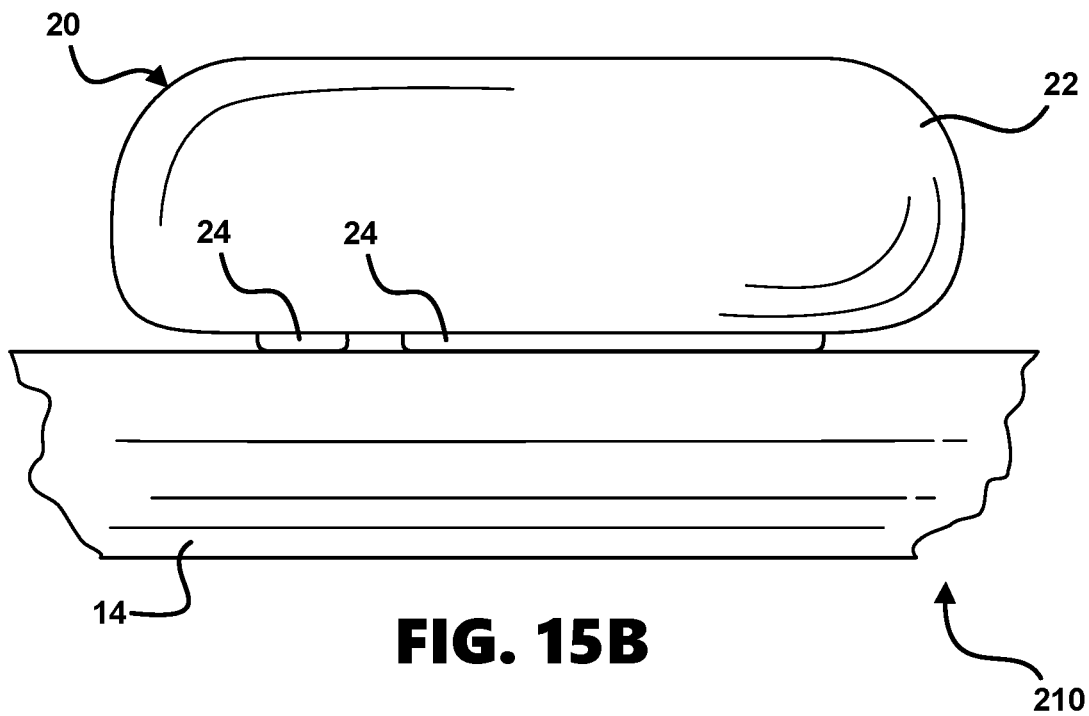
Figure 16A:
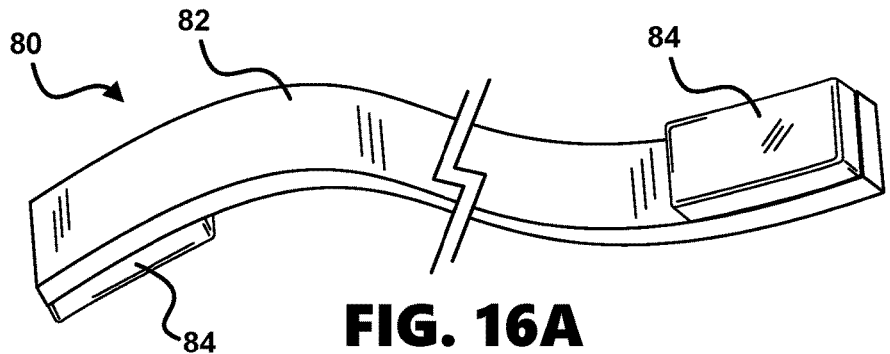
FIG. 16A is a perspective view of a releasable band shown in a contoured position.
Figure 16B:
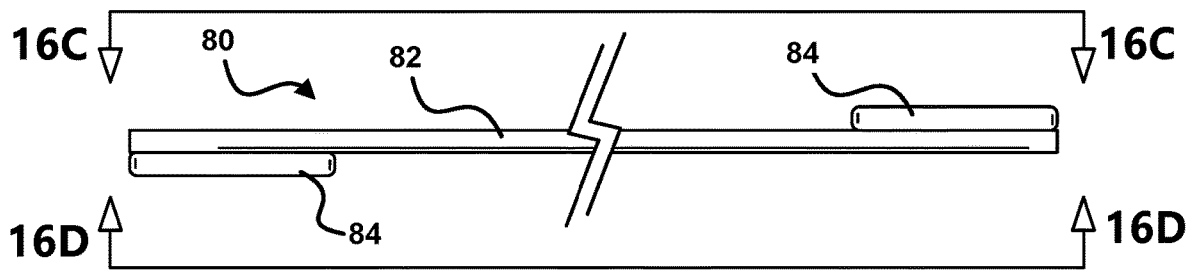
FIG. 16B is a side elevation view of the releasable band of FIG. 16A shown in a straightened position.
Figure 16C:
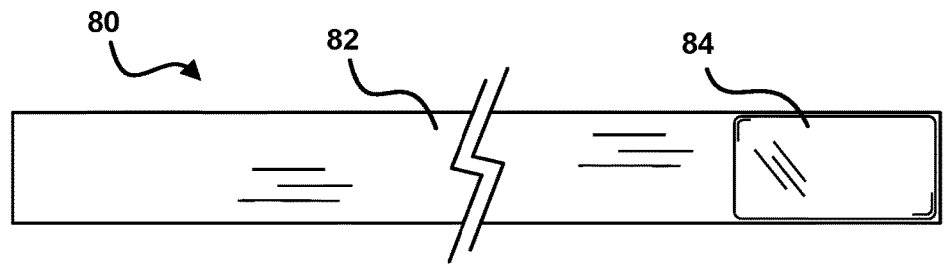
FIG. 16C is a top plan view of the releasable band of FIG. 16A taken along line 16C-16C of FIG. 16B.
Figure 16D:
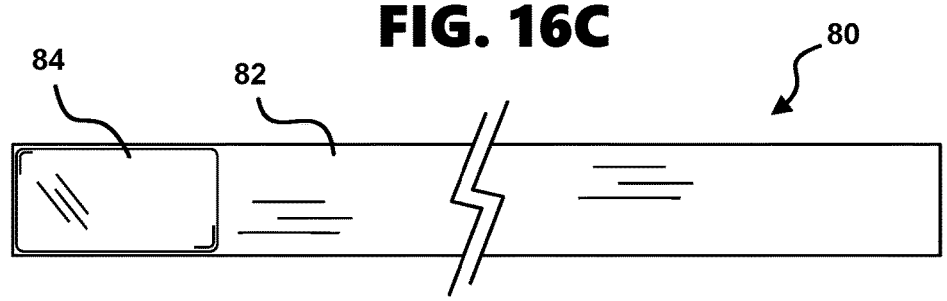
FIG. 16D is a bottom plan view of the releasable band of FIG. 16A taken along line 16D-16D of FIG. 16B.

Referring to FIGS. 14, 15A and 15B a third user examination table assembly 210 is shown which does not include the fifth gel elastomer sheet 32 or sixth gel elastomer sheet 52. The U-shaped positioning device 20, the rectangular prism shaped positioning device 40, and the channel shaped positioning device 60 are provided to be releasably connectable to a surface for example the tabletop 14. The U-shaped positioning device 20 as shown by the arrows 202, 204 is releasably attached directly to the tabletop 14 via the first gel elastomer sheet 24. The rectangular prism shaped positioning device 40 and the channel shaped positioning device 60 also are releasably attached directly to the tabletop 14 respectively via the second gel elastomer sheet 44 and the third gel elastomer sheet 64. The first gel elastomer sheet 24, the second gel elastomer sheet 44, and the third gel elastomer sheet 64 provide suitable tackiness to enable adhesion to the tabletop 14, which tabletop 14 preferably has a smooth surface to facilitate adhesion. Alternatively, the U-shaped positioning device 20, the rectangular prism shaped positioning device 40, and the channel shaped positioning device 60 can be adhered to a multitude of surfaces other than the tabletop 14 respectively via the first gel elastomer sheet 24, the second gel elastomer sheet, 44, and the third gel elastomer sheet 64.

Referring to FIGS. 16A-16D, a releasable band 80 is shown for example for use in securing or positioning a patient during medical or palliative treatments or procedures. The releasable band 80 includes an elongated pliable material strip 82 which can include polyester webbing, nylon webbing, or other flexible woven or non-woven material. At each end of the elongated pliable material strip 82 there is a gel elastomer piece 84 connected to the elongated pliable material strip 82. Each of the gel elastomer pieces 84 is connected to an opposite surface of the elongated pliable material strip 82.

Figure 17:
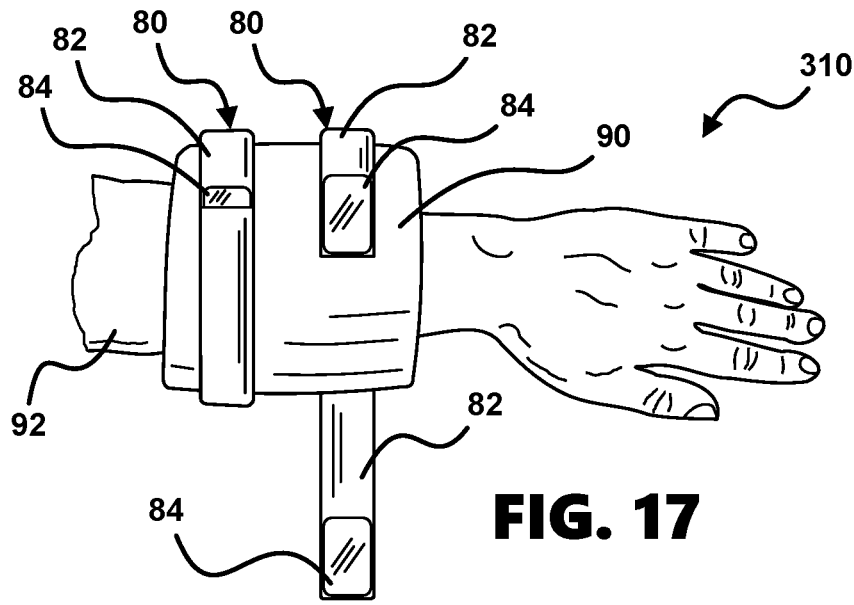
FIG. 17 is a top plan view of a user positioning setup including the releasable band of FIG. 16A.
Figure 18A:
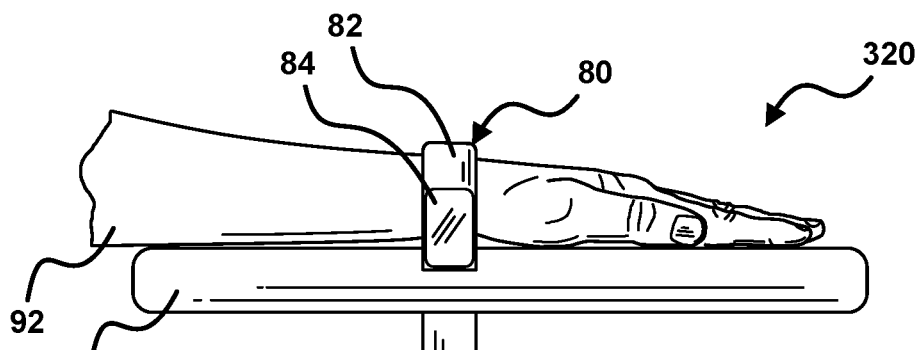
FIGS. 18A and 18B are side elevation views of other user positioning setups including the releasable band of FIG. 16A shown unsecured and secured respectively.
Figure 18B:
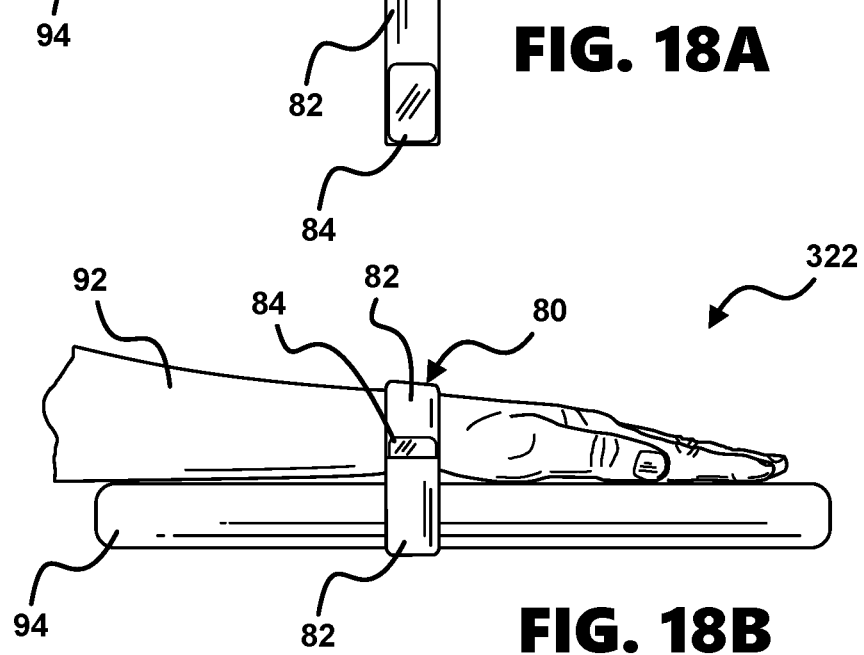

Referring to FIGS. 17, 18A, 18B, example uses of the releasable band 80 are shown with reference to a first user positioning setup 310, a second user positioning setup 320, and a third user positioning setup 322. In the first user positioning setup 310, a first platform in the form of a cylindrical ice pack 90 is secured to an arm 92 of a user by wrapping two releasable bands 80 around the ice pack 90 and the arm 92. One of the releasable bands 80 is shown just prior to connecting the gel elastomer pieces 84 together, and one of the releasable bands 80 is shown with its gel elastomer pieces 84 connected together securing the ice pack 90 to the arm 92.

In the second user positioning setup 320, a second platform in the form of a rectangular prism board 94 is in the process of being secured to the arm 92 of the user by the releasable band 80. In the third user positioning setup 322, the rectangular prism board 94 is shown secured to the arm 92 of the user by wrapping the releasable band 80 around the rectangular prism board 94 and the arm 92 and connecting the gel elastomer pieces 84. The rectangular prism board 94 can be fixedly attached to a stable surface such as a hospital bed or can be freestanding in the form of a splint.

Figure 19A:
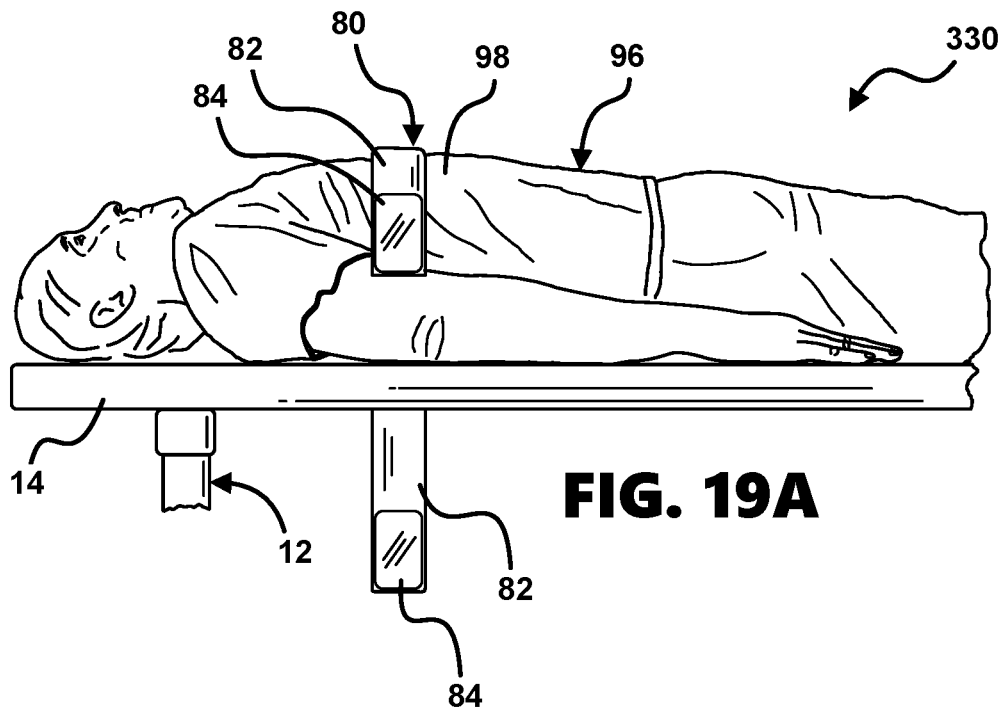
FIGS. 19A and 19B are side elevation views of yet other user positioning setups including the releasable band of FIG. 16A shown unsecured and secured respectively.
Figure 19B:
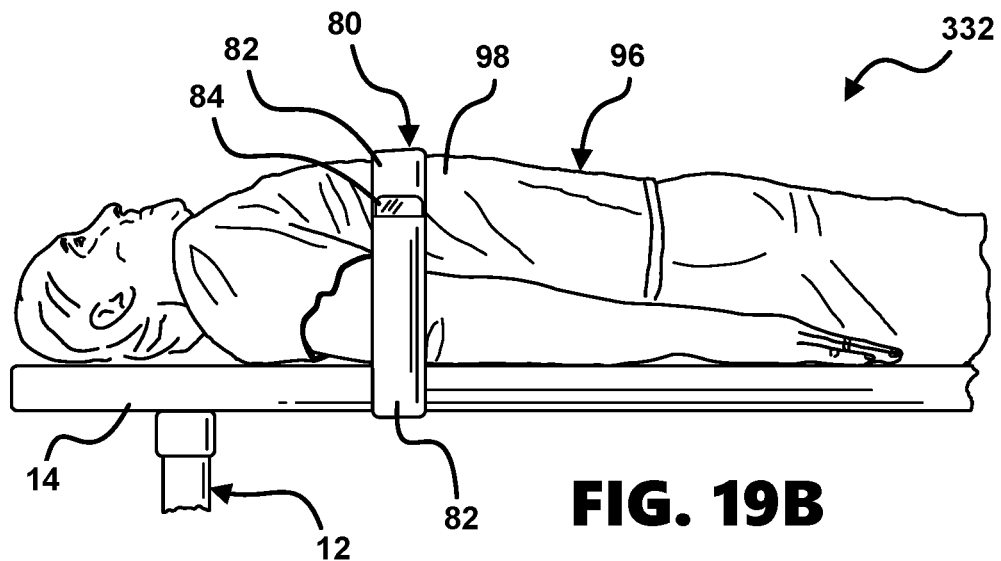

Referring to FIGS. 19A and 19B, further example uses of the releasable band 80, depicted appropriately up-scaled, are shown with reference to a fourth user positioning setup 330 and a fifth user positioning setup 332. In the fourth user positioning setup 330, the torso 98 of a user 96 is in the process of being secured to a third platform in the form of the tabletop 14 by the releasable band 80. In the fifth user positioning setup 332, the user 96 is shown secured to the tabletop 14 by wrapping the releasable band 80 around the torso 98 of the user 96 and the tabletop 14 and connecting the gel elastomer pieces 84.

Referring to FIG. 22, the releasable band 80 supports the performance of a method 400 for connecting a user to a platform. The method 400 is described with reference to the releasable band 80 and the first user positioning setup 310, the second user positioning setup 320, the third user positioning setup 322, the fourth user positioning setup 330, and the fifth user positioning setup 332. Alternatively, the method 400 can be performed with other bands other than the releasable band 80 in other operating environments. The method 400 includes providing a band including an elongated pliable material strip including a first end and a second end, a first elastomer gel piece connected to the first end of the elongated pliable material strip, and a second elastomer gel piece connected to the second end of the elongated pliable material strip (step 402). A platform is provided (step 404), and the user is positioned on the platform (step 406). The band is wrapped around the platform and the user (step 408), and the second elastomer gel piece is releasably connected to the first elastomer gel piece (step 410). The platform can include for example an ice pack, a table, an arm rest, a leg rest, or a splint. Positioning the user on the platform can include positioning an appendage, or a torso, or a combination of one or more appendages and a torso of the user on the platform. Wrapping the band around the platform and the user can include wrapping the band around an appendage, or a torso, or a combination of one or more appendages and a torso of the user on the platform.

Referring to FIGS. 20A and 20B, a sixth user positioning setup 340 and a seventh user positioning setup 342 are shown. The first positioning apparatus 21 including the U-shaped positioning device 20, the fifth gel elastomer sheets 32, and the fifth adhesive layers 34 is attached to the tabletop 14 which is part of a tilting examination table 112. The U-shaped positioning device 20 supports a head 97 of the user 96. Two of the second positioning apparatuses 41 each including the rectangular prism shaped positioning device 40, the sixth gel elastomer sheet 52, and the sixth adhesive layer 54 are further attached to the tabletop 14. Each of the rectangular prism shaped positioning devices 40 supports a leg 99 of the user 96. The fifth adhesive layer 34 secures three of the fifth gel elastomer sheets 32 to the tabletop 14, and the U-shaped positioning device 20 is releasably connected to the fifth gel elastomer sheets 32 via first gel elastomer sheets 24. Two of the sixth adhesive layers 54 respectively secure two of the sixth gel elastomer sheets 52 to the tabletop 14, and two of the rectangular prism shaped positioning devices 40, one for each leg 99, are releasably connected to the sixth gel elastomer sheets 52 via two of the second gel elastomer sheets 44. The user 96 is secured to the tabletop 14 by wrapping the releasable band 80 around the torso 98 of the user 96 and the tabletop 14 and connecting together the gel elastomer pieces 84 of the releasable band 80.

Further referring to FIGS. 20A and 20B, at a plurality of angles A, shear forces F are induced by the weights of the user 96, the U-shaped positioning device 20 and the rectangular prism shaped positioning devices 40. The shear forces F are resisted by adhesion between the first gel elastomer sheets 24 and the fifth gel elastomer sheets 32 and also between the second gel elastomer sheets 44 and the sixth gel elastomer sheets 52 to maintain the user 96, the U-shaped positioning device 20, and the rectangular prism shaped positioning devices 40 in a static position.

Referring to FIGS. 21A and 21B, an eighth user positioning setup 350 and a ninth user positioning setup 352 are shown. The U-shaped positioning device 20 is attached to the tabletop 14 which is part of the tilting examination table 112. The U-shaped positioning device 20 supports the head 97 of the user 96. Two of the rectangular prism shaped positioning devices 40 are further attached to the tabletop 14. Each of the rectangular prism shaped positioning devices 40 supports a leg 99 of the user 96. The U-shaped positioning device 20 is releasably connected to the tabletop 14 via the first gel elastomer sheets 24. The rectangular prism shaped positioning devices 40 are releasably connected to the tabletop 14 respectively via two of the second gel elastomer sheets 44. The user 96 is secured to the tabletop 14 by wrapping the releasable band 80 around the torso 98 of the user 96 and the tabletop 14 and connecting together the gel elastomer pieces 84 of the releasable band 80.

Further referring to FIGS. 21A and 21B, at a plurality of angles A, shear forces F are induced by the weights of the user 96, the U-shaped positioning device 20 and the rectangular prism shaped positioning device 40. The shear forces F are resisted by adhesion between the first gel elastomer sheets 24 and the tabletop 14 and also between the second gel elastomer sheet 44 and the tabletop 14 to maintain the user 96, the U-shaped positioning device 20, and the rectangular prism shaped positioning device 40 in a static position.

Referring to FIG. 23, the first positioning apparatus 21, U-shaped positioning device 20, second positioning apparatus 41, rectangular prism shaped positioning device 40, third positioning apparatus 61, and channel shaped positioning device 60 support the performance of a user positioning method 500. The method 500 is described with reference to the first, second, and third user examination table assemblies 10, 110, 210 and the first, second, third, sixth, seventh, eighth, and ninth user positioning setups 310, 320, 322, 340, 342, 350, 352. Alternatively, the method 500 can be performed with other user positioning setups in other operating environments.

The method 500 includes providing a malleable pad including a first gel elastomer (step 502). A platform is provided (step 504), and the malleable pad is connected to the platform via the first gel elastomer (step 506). A user is provided (step 508), and a body part of the user is positioned on the malleable pad (step 510). A second gel elastomer can also be provided, and a first adhesive layer can be connected to the second gel elastomer. The second gel elastomer can be connected to the platform via the first adhesive layer, and the first gel elastomer can be connected to the second gel elastomer to connect the malleable pad to the platform. A first film can be releasably connected to the first adhesive layer which first film is removed prior to connecting the second gel elastomer to the platform via the first adhesive layer. A second film can be releasably connected to a surface of the second gel elastomer and a third film can be releasably connected to a surface of the first gel elastomer which second and third films can both be removed prior to connecting the first gel elastomer to the second gel elastomer. Providing the malleable pad including the first gel elastomer can include providing a second adhesive layer connected to the first gel elastomer, providing a fourth film releasably connected to the second adhesive layer, providing a foam form, removing the fourth film to expose the second adhesive layer, and connecting the first gel elastomer to the foam form via the second adhesive layer.

Each of the gel elastomers described herein ("the gel elastomer"), including the first through eighth gel elastomer sheets 24, 44, 64, 144, 32, 52, 152, 72 and the gel elastomer pieces 84, preferably include a polyurethane gel elastomer formulated as a cross-linked system that maintains its shape while being stretched or compressed in any direction. The cross-linked structure of the system preferably provides high elasticity with high tensile strength. Alternatively, the gel elastomer can include a silicone gel elastomer.

The gel elastomer is preferably stable, non-toxic, and non-irritating and preferably does not include latex, silicone, plasticizers or phthalates. The gel elastomer is formulated to not harden over time and to be non-porous so that it will not absorb liquids. Further, the gel elastomer is formulated to be resistant to oils (e.g., skin oils), greases, and common medical ointments.

The gel elastomer is produced as a reaction product of a two-part, A-side isocyanate and B-side polyol, cross-linked ether-based polyurethane system. More particularly, the gel elastomer is a reaction product of a composition including an A-side including an isocyanate prepolymer, preferably a methylene diphenyl isocyanate ("MDI") prepolymer, and a B-side including a polyether polyol. The A-side and B-side of the system are metered and mixed into one to produce the gel elastomer as a semi-solid sticky substance.

The ratios for producing the gel elastomer are as follows: 5% to 45% of the weight of the composition is the A-side including the MDI prepolymer, and 95% to 55% of the weight of the composition is the B-side including the polyether polyol. More ideal ratios for producing the gel elastomer are as follows: 20% to 40% of the weight of the composition is the A-side including the MDI prepolymer, and 80% to 60% of the weight of the composition is the B-side including the polyether polyol to achieve the ideal hardness and ideal level of tack and stickiness.

The polyether polyol is preferably a polyoxypropylene triol modified with ethylene oxide and having a molecular weight range of 4650 to 5000. The polyether polyol is ideally a polyoxypropylene triol modified with ethylene oxide and having a molecular weight of 4800.

The MDI prepolymer preferably has a free NCO content that ranges from 2% to 20% by weight. Ideally the MDI prepolymer has a free NCO content that ranges from 2.4% to 4.9% by weight. NCO content as described herein refers to a value as determined according to DIN EN ISO 11909.

A catalyst can be used for promoting a quicker reaction or cure time of the two-part isocyanate and polyol system. A single catalyst or a combination of two or more catalysts can be used to form the reaction product including for example tertiary amines and organometallic compounds. The organometallic compounds can include for example organotin and organobismuth compounds.

In an alternative implementation, an ester-based polyurethane two-part system that utilizes an MDI prepolymer can be provided to produce the gel elastomer, wherein the gel elastomer includes a reaction product of a composition including an isocyanate prepolymer and a polyester polyol, and the isocyanate prepolymer includes an MDI prepolymer.

EXAMPLE

To facilitate understanding of the gel elastomer, referring to Table 1, an example of an illustrative embodiment of the gel elastomer is provided, which example is not intended to identify key features or essential features of the claimed subject matter and is not intended to be used to limit the scope of the claimed subject matter. All percentages referred to in the example of Table 1 refer to weight percent.

TABLE 1

| Weight | Component |
|---|---|
| A side 30% | MDI prepolymer with 3.7% free NCO content |
| B side 70% | Polyoxypropylene triol modified with ethylene oxide and having a molecular weight of 4800 |

Although features and elements are described above in particular combinations, one of ordinary skill in the art will appreciate that each feature or element can be used alone or in any combination with the other features and elements. While embodiments have been described in detail above, these embodiments are non-limiting and should be considered as merely exemplary. Modifications and extensions may be developed, and all such modifications are deemed to be within the scope defined by the appended claims.

What is claimed is:

1. A user positioning apparatus comprising:
   a malleable pad comprising a first gel elastomer;
   a second gel elastomer releasably connectable to the malleable pad via the first gel elastomer; and
   a first adhesive layer connected to the second gel elastomer.

2. The apparatus of claim 1, further comprising a film releasably connected to the first adhesive layer.

3. The apparatus of claim 1, wherein the malleable pad forms a channel.

4. The apparatus of claim 1, wherein the malleable pad forms a U shape.

5. The apparatus of claim 1, wherein the malleable pad forms a rectangular prism.

6. The apparatus of claim 1, the malleable pad further comprising foam connected to the first gel elastomer.

7. The apparatus of claim 6, the foam comprising polyurethane foam.

8. The apparatus of claim 6, wherein:
   the foam is formed as a channel; and
   the first gel elastomer comprises a sheet connected to the channel.

9. The apparatus of claim 6, wherein:
   the foam is formed as a U shape; and
   the first gel elastomer comprises a sheet connected to the U Shape.

10. The apparatus of claim 6, wherein:
    the foam is formed as a rectangular prism; and
    the first gel elastomer comprises a sheet connected to the rectangular prism.

11. The apparatus of claim 6, wherein the foam is connected to the first gel elastomer via a second adhesive layer.

12. The apparatus of claim 11, wherein the second adhesive layer comprises an acrylic adhesive.

13. The apparatus of claim 1, wherein the first adhesive layer comprises a pressure sensitive adhesive ("PSA").

14. The apparatus of claim 1, wherein the first gel elastomer and the second gel elastomer each comprise a polyurethane gel elastomer.

15. The apparatus of claim 1, wherein the first gel elastomer and the second gel elastomer each comprise a silicone gel elastomer.

16. The apparatus of claim 1, wherein at least one of the first gel elastomer or the second gel elastomer comprise a reaction product of a composition comprising an A-side comprising an isocyanate prepolymer and a B-side comprising a polyether polyol.

17. The apparatus of claim 16, wherein the A-side comprises between 5% and 45% of the weight of the composition.

18. The apparatus of claim 16, wherein the A-side comprises between 20% and 40% of the weight of the composition.

19. The apparatus of claim 1, wherein at least one of the first gel elastomer or the second gel elastomer comprises a reaction product of a composition comprising an isocyanate prepolymer and a polyether polyol.

20. The apparatus of claim 19, wherein the isocyanate prepolymer comprises a methylene diphenyl isocyanate ("MDI") prepolymer.

21. The apparatus of claim 20, wherein the polyether polyol comprises a polyoxypropylene triol modified with ethylene oxide and having a molecular weight between 4650 and 5000.

22. The apparatus of claim 19, wherein a free NCO content in the isocyanate prepolymer ranges from 2% to 20%.

23. The apparatus of claim 19, wherein a free NCO content in the isocyanate prepolymer ranges from 2.4% to 4.9%.

24. The apparatus of claim 19, wherein the composition further comprises at least one catalyst.

25. The apparatus of claim 24, wherein the at least one catalyst comprises at least one of a tertiary amine or an organometallic compound.

26. The apparatus of claim 1, wherein the first gel elastomer and the second gel elastomer are identically formulated polyurethane gel elastomers.

27. The apparatus of claim 1, wherein at least one of the first gel elastomer or the second gel elastomer comprises a reaction product of a composition comprising an isocyanate prepolymer and a polyester polyol, wherein the isocyanate prepolymer comprises an MDI prepolymer.

28. The apparatus of claim 1, the first gel elastomer and the second gel elastomer comprising a reaction product of a composition comprising an isocyanate prepolymer and a polyether polyol.

29. The apparatus of claim 28, wherein:
    the isocyanate prepolymer comprises a methylene diphenyl isocyanate ("MDI") prepolymer having a free NCO content that ranges from 2.4% to 4.9%; and
    the polyether polyol comprises a polyoxypropylene triol modified with ethylene oxide and having a molecular weight between 4650 and 5000.

30. The apparatus of claim 29, wherein:
    the isocyanate prepolymer comprises between 20% by weight and 40% by weight of the composition; and
    the polyether polyol comprises between 80% by weight and 60% by weight of the composition.

31. A user positioning method comprising:
    providing an apparatus comprising a malleable pad comprising a first gel elastomer, a second gel elastomer releasably connectable to the first malleable pad via the first gel elastomer, and a first adhesive layer connected to the second gel elastomer;
    providing a platform;
    connecting the second gel elastomer to the platform via the first adhesive layer;
    connecting the first gel elastomer to the second gel elastomer to connect the malleable pad to the platform;
    providing a user; and
    positioning a body part of the user on the malleable pad.

32. The method of claim 31, further comprising:
providing a film releasably connected to the first adhesive layer; and
removing the film to expose the first adhesive layer prior to connecting the second gel elastomer to the platform.

33. The method of claim 31, further comprising:
providing a first film releasably connected to the first adhesive layer and a second film releasably connected to a surface of the second gel elastomer;
removing the first film to expose the first adhesive layer prior to connecting the second elastomer to the platform; and
removing the second film to expose the second gel elastomer prior to connecting the first gel elastomer to the second gel elastomer.

34. The method of claim 33, further comprising:
providing a third film releasably connected to a surface of the first gel elastomer; and
removing the third film to expose the first gel elastomer prior to connecting the first gel elastomer to the second gel elastomer.

35. The method of claim 34, wherein providing the malleable pad comprising the first gel elastomer comprises:
providing a second adhesive layer connected to the first gel elastomer;
providing a fourth film releasably connected to the second adhesive layer;
providing a foam form;
removing the fourth film to expose the second adhesive layer; and
connecting the first gel elastomer to the foam form via the second adhesive layer.

* * * * *